(12) United States Patent
Shalwitz

(10) Patent No.: US 10,946,034 B2
(45) Date of Patent: *Mar. 16, 2021

(54) METHODS FOR THE USE OF 5'-ADENOSINE DIPHOSPHATE RIBOSE (ADPR)

(71) Applicant: Invirsa, Inc., Columbus, OH (US)

(72) Inventor: Robert Shalwitz, Bexley, OH (US)

(73) Assignee: Invirsa, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,760

(22) Filed: Mar. 26, 2019

(65) Prior Publication Data

US 2019/0298752 A1 Oct. 3, 2019

Related U.S. Application Data

(60) Provisional application No. 62/648,585, filed on Mar. 27, 2018, provisional application No. 62/693,021, filed on Jul. 2, 2018.

(51) Int. Cl.
| | | |
|---|---|---|
| *A01N 43/04* | (2006.01) |
| *A61K 31/70* | (2006.01) |
| *A61K 31/7076* | (2006.01) |
| *A61P 31/22* | (2006.01) |
| *A61P 31/14* | (2006.01) |
| *A61P 11/00* | (2006.01) |
| *A61K 9/00* | (2006.01) |
| *A61K 31/7056* | (2006.01) |
| *A61K 47/02* | (2006.01) |
| *A61P 31/12* | (2006.01) |

(52) U.S. Cl.
CPC ............ *A61K 31/7076* (2013.01); *A61K 9/00* (2013.01); *A61K 9/0014* (2013.01); *A61K 9/0019* (2013.01); *A61K 9/0053* (2013.01); *A61K 31/7056* (2013.01); *A61K 47/02* (2013.01); *A61P 11/00* (2018.01); *A61P 31/12* (2018.01); *A61P 31/14* (2018.01); *A61P 31/22* (2018.01)

(58) Field of Classification Search
None
See application file for complete search history.

(56) References Cited

U.S. PATENT DOCUMENTS

| 6,331,529 B1 | 12/2001 | Yerxa et al. |
|---|---|---|
| 6,436,910 B1 | 8/2002 | Yerxa et al. |
| 6,528,042 B1 | 3/2003 | Brown et al. |
| 6,989,260 B2 | 1/2006 | Christenson et al. |
| 7,115,585 B2 | 10/2006 | Yerxa et al. |
| 2002/0052338 A1 | 5/2002 | Yerxa et al. |
| 2003/0008834 A1 | 1/2003 | Yerxa et al. |
| 2003/0236217 A1 | 12/2003 | Shalwitz et al. |
| 2005/0009777 A1 | 1/2005 | Mack et al. |
| 2005/0276762 A1 | 12/2005 | Das |
| 2007/0212395 A1 | 9/2007 | Donello et al. |
| 2008/0081796 A1 | 4/2008 | Shalwitz et al. |
| 2008/0305994 A1 | 12/2008 | Zhang et al. |
| 2011/0217262 A1 | 9/2011 | Kornfield et al. |
| 2013/0116284 A1 | 5/2013 | Salzman |
| 2015/0038473 A1 | 2/2015 | Stein et al. |

FOREIGN PATENT DOCUMENTS

| EP | 0701562 B1 | 6/1997 |
|---|---|---|
| EP | 1948215 B1 | 1/2012 |
| EP | 2647382 A1 | 10/2013 |
| JP | H 07247210 | 9/1995 |
| WO | WO 2017/143113 A1 | 8/1917 |
| WO | WO 1999/12951 | 3/1999 |
| WO | WO 2003/072067 A1 | 9/2003 |
| WO | WO 2003/099297 A1 | 12/2003 |
| WO | WO 2005/123030 A1 | 12/2005 |
| WO | WO 2006/127987 A2 | 11/2006 |
| WO | WO 2007/054814 A1 | 5/2007 |
| WO | WO 2015/073319 A1 | 5/2015 |

OTHER PUBLICATIONS

Griffiths et al. Clinical Microbiology Reviews (2017), vol. 30, pp. 277-319.*
Blumberg et al., 1989, "Herpes Zoster," Clinics in Dermatology, 7(1):37-48.
Nikkels et al., 1994, "Recognition and Treatment of Shingles," Drugs, 48(4):529-548.
Haile et al., 2011, "The Activity of an Ancient Atypical Protein Kinase is Stimulated by ADP-Ribose in vitro," Archives of Biochemistry & Biophysics, 511:56-63.
Malanga et al., 1998, "Polu(ADP-Ribose) Binds to Specific Domains of p53 and Alters its DNA Binding Functions," Journal of Biological Chemistry, 273(19):11839-11843.
International Search Report dated Oct. 28, 2019 of International Application No. PCT/US2019/023977.
Written Opinion dated Oct. 28, 2019 of International Application No. PCT/US2019/023977.
Bawage et al., 2013, "Recent Advances in Diagnosis, Prevention, and Treatment of Human Respiratory Synctial Virus", Advances in Virology, 203:1-26.
Aleo et al., 1996, "Enzymatic activites affecting exogenous nicotinamide adenine dinucleotide in human skin fibroblasts", J Cell Physiol, 167:173-176.
Braun, 2014, "A novel disease connection for TRPM2 channels", Channels, 8(6):475-476.
Clement et al., 2011, "Clinical and antiviral efficacy of an ophthalmic formulation of dexamethasone povidone-iodone in a rabbit model of adenoviral keratoconjunctivitis", Investigative Ophthalmology & Visual Science, 52(1):339-344.

(Continued)

*Primary Examiner* — Patrick T Lewis
(74) *Attorney, Agent, or Firm* — Jones Day

(57) ABSTRACT

The present invention is directed to methods for the use of 5'-adenosine diphosphate ribose (ADPR), and compositions thereof, for treating, managing, or preventing RNA virus-related diseases or conditions, herpes virus related diseases or conditions, Sirtuin 6 (Sirt6)-related diseases or conditions, Pax6 related diseases or conditions, and p53 related diseases or conditions.

23 Claims, 14 Drawing Sheets

(56) References Cited

OTHER PUBLICATIONS

Gil-Fernández et al., 1987, "Antiviral activity of uridine 5'-diphosphate glucose analogues against some enveloped viruses in cell culture", Antiviral Research, 8:299-310.
Hottiger, 2015, SnapShot: ADP-ribosylation signaling, Molecular Cell, 58:1134.
Houlsby et al., 1986, "Antimicrobial activity of borate-buffered solutions", Antimicrobial Agents and Chemotherapy, 29(5):803-806.
Huang et al., 2014, Extracellular ADP-ribose induces [Ca2+] pathway in pulmonary artery smooth muscle cells, FASEB J, 28(1):Suppl 1175.4.
Im and Hoopes, 1989, "Improved skin flap survival with nicotinic acid and nicotinamide in rats", J Surg Res, 47:453-455.
International Search Report dated May 29, 2017 of International Application No. PCT/US2017/018253.
Johns et al., 2007, "Cytoprotective agent in lactobacillus bulgaricus extracts", Current Microbiology, 54(2):131-135.
Lin et al., 2012, "Niacinamide mitigated the acute lung injury induced by phorbol myristate acetate in isolated rat's lungs", J Biomed Sci, 19(27):1-13.
Lion, 2014, "Adenovirus infections in immunocompetent and immunocompromised patients", Clin Microbiol Rev, 27(3):441-462.
Martínez-Aguado et al., 2015, "Antiadenovirus drug discovery: potential targets and evaluation methodologies", Drug Discovery Today, 20(10):1235-1242.
Neurath et al., 1970, "Disruption of adenovirus type 7 by lithium iodide resulting in the release of viral deoxyribonucleic acid", J Virol, 5(2):173-178.
Paoletti et al., 2012, "Multifaceted roles of purinergic receptors in viral infection", Microbes and Infection, 14(14):1278-1283.
Van Groeningen et al., 1992, "Modulation of fluorouracil toxicity with uridine", Seminars in Oncology, 19(2)Suppl 3:148-154.
Virág and Szabó, 2002, "The therapeutic potential of poly (ADP-ribose) polymerase inhibitors", Phamacol Rev, 54(3):375-429.
Wright et al., 2016, "ADP-ribose-derived nuclear ATP synthesis by NUDIX5 is required for chromatin remodeling", Science, 352(6290):1221-1225.
Written Opinion dated May 29, 2017 of International Application No. PCT/US2017/018253.
Budayeva et al., 2015, "The intricate roles of mammalian sirtuins in defense against viral pathogens," J. Virol., 90(1):5-8.
Chen et al., 2013, "Pax6 Downregulation Mediates Abnormal Lineage Commitment of the Ocular Surface Epithelium in Aqueous-Deficient Dry Eye Disease," PLoS One, 8(10):e77286.
Koyuncu et al., 2014, "Sirtuins Are Evolutionarily Conserved Viral Restriction Factors," Mbio, 5(6):e02249-14.
Li et al., 2008, "Down-regulation of Pax6 is associated with abnormal differentiation of corneal epithelial cells in severe ocular surface diseases," J. Pathol., 214(1):114-122.
McNamara et al., 2014, "Establishing PAX6 as a Biomarker to Detect Early Loss of Ocular Phenotype in Human Patients With Sjogren's Syndrome," Invest. Ophthalmol Vis. Sci., 55:7079-7084.
Pan et al., 2011, "Structure and Biochemical Functions of SIRT6," J. Biol. Chem., 286(16):14575-14587.
Khan et al., 2006, "Use of Substrate Analogs and Mutagenesis to Study Substrate Binding and Catalysis in the Sir2 Family of NAD-dependent Protein Deacetylases," J. Biol. Chem., 281(17): 11702-11711.
Priest et al., 2010, "Deconstructing nucleotide binding activity of the Mdm2 RING domain," Nucleic Acids Res., 38(21):7587-7598.
Poyurovsky et al., 2003, "Nucleotide Binding by the MDM2 Ring Domain Facilitates Arf-Independent MDM2 Nucleolar Localization," Mol. Cell, 12(4):875-887.
Zhang et al., 2014, "Aberrant activation of p53 due to loss of MDM2 or MDMX causes early lens dysmorphogenesis," Dev. Biol., 396(1):19-30.
Thirumurthi et al., 2014, "MDM2-mediated degradation of SIRT6 phosphorylated by AKT1 promotes tumorigenesis and trastuzumab resistance in breast cancer," Sci. Signal, 7(336):ra71.

\* cited by examiner (a)

(b)

(a)

(b)

(c)

METHODS FOR THE USE OF 5'-ADENOSINE DIPHOSPHATE RIBOSE (ADPR)

CROSS-REFERENCES TO RELATED APPLICATIONS

This application claims the benefit of U.S. Provisional Patent Application No. 62/648,585, filed Mar. 27, 2018, and U.S. Provisional Patent Application No. 62/693,021, filed Jul. 2, 2018, each of which is incorporated herein by reference in its entirety.

1 FIELD OF THE INVENTION

The present invention is directed to methods for the use of 5'-adenosine diphosphate ribose (ADPR), and compositions thereof, for treating, managing, or preventing RNA virus-related diseases or conditions, herpes virus related diseases or conditions, Sirtuin 6 (Sirt6)-related diseases or conditions, Pax6 related diseases or conditions, and p53 related diseases or conditions.

2 BACKGROUND OF THE INVENTION

An RNA virus is a virus that has RNA (ribonucleic acid) as its genetic material. This nucleic acid is usually single-stranded RNA (ssRNA) but may be double-stranded RNA (dsRNA). Notable human diseases caused by RNA viruses include bronchitis and bronchiolitis (human respiratory syncytial virus and others), hemorrhagic fever (Ebola virus and others), severe acute respiratory syndrome (coronavirus), the common cold (rhinovirus, parainfluenza virus, corona virus, and others), influenza, hepatitis C, West Nile fever, polio, measles, and acquired immunodeficiency syndrome (human immunodeficiency virus).

Human respiratory syncytial virus (HRSV) is a well-established infectious agent in both immunocompetent as well as immunocompromised individuals. HRSV is a single stranded, negative sense, RNA virus. HRSV typically causes respiratory tract infections that effect all portions of the respiratory tract. HRSV is major cause of lower respiratory tract disease, bronchiolitis and pneumonia, in infants and children. In the United States, 60% of infants are infected during their first RSV season, and nearly all children will have been infected with the virus by 2-3 years of age. Of those infected with HRSV, 2-3% will develop bronchiolitis, necessitating hospitalization. Natural infection with HRSV induces protective immunity which wanes over time— possibly more so than other respiratory viral infections—and thus people can be infected multiple times. Sometimes an infant can become symptomatically infected more than once, even within a single HRSV season. Severe HRSV infections have increasingly been found among elderly patients. Young adults can be re-infected every five to seven years, with symptoms typically looking like a sinus infection or a cold (infections can also be asymptomatic). The incubation time (from infection until symptoms arrive) is 4-5 days. For adults, HRSV produces mainly mild symptoms, often indistinguishable from common colds and minor illnesses. The Centers for Disease Control consider HRSV to be the most common cause of bronchiolitis (inflammation of the small airways in the lung) and pneumonia in children under 1 year of age in the United States (Hall et al., 2009, N. Engl. J. Med., 360(6):588-598; Iwane et al., 2013, J. Infect. Dis., 208(Suppl. 3): 2-3; Rose et al., 2018, Respiratory Syncytial Virus Seasonality—United States, 2014-2017, MMWR Morb. Mortal Wkly. Rep., 67:71-76). For some children, HRSV can cause bronchiolitis, leading to severe respiratory illness requiring hospitalization and, rarely, causing death. This is more likely to occur in patients that are immunocompromised, or infants born prematurely. Other HRSV symptoms common among infants include listlessness, poor or diminished appetite, and a possible fever. According to a study by Falsey (Falsey et al., 2005, N. Engl. J. Med., 352(17):1749-1759), over four winter respiratory seasons in Rochester, N.Y. (1999-2003), HRSV infection developed annually in an average of 5.5 percent (range, 3 to 7 percent) of healthy adults age 65 years and older (i.e., without COPD or CHF) and 4 to 10 percent of high-risk adults age 21 years and older (i.e., diagnosed with chronic heart or lung disease). In this same population, HRSV was responsible for 9.6 percent of these hospitalizations. Based on discharge diagnosis, HRSV accounted for 10.6 percent of hospitalizations for pneumonia, 11.4 percent for chronic obstructive pulmonary disease (COPD), 7.2 percent for asthma, and 5.4 percent for congestive heart failure (CHF). In adults, age 65 and over, HRSV infection, based on data from the Centers for Disease Control and Prevention (CDC), is estimated to cause 14,000 annual deaths in US adults.

Herpesviridae is a large family of DNA viruses that cause diseases in animals and humans. The members of this family are also known as herpes viruses. The Greek derivation of the herpes name refers to the latent, recurring infections typical of this group of viruses. Herpes viuses can cause latent or lytic infections. At least five species of Herpes viruses—herpes simplex virus 1 and 2 (known as HSV-1 and HSV-2), varicella zoster virus (the cause of chickenpox and shingles), Epstein-Barr virus (implicated in several diseases, including mononucleosis and some cancers), and cytomegalovirus—are extremely widespread among humans. More than 90% of adults have been infected with at least one of these, and a latent form of the virus remains in most people. There are 9 herpes virus types known to infect humans: HSV-1 and HSV-2, (also known as HHV1 and HHV2), varicella-zoster virus (VZV, which may also be called by its ICTV name, HHV-3), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV, also known as HHV-8).

Reduced activity of the protein sirtuin 6 (Sirt6) has been associated with multiple diseases, such as viral diseases, diseases due to aging, diabetes mellitus, type 2 diabetes mellitus, respiratory disorders, chronic lung disease, chronic obstructive pulmonary disease, asthma, idiopathic pulmonary fibrosis, cystic fibrosis, ocular disorders, diabetic retinopathy, retinal disease, retinal detachment, adult macular degeneration, glaucoma, liver disease, non-alcoholic steatohepatitis, chronic hepatitis infection, neurodegenerative disorders (e.g., Alzheimer's disease), disorders resulting in cognitive decline, trauma resulting in brain or spinal cord injury, cancer, a chemotherapy-induced neuropathy, neuropathy associated with an ischemic or traumatic event, an autoimmune disorder, disorders associated with excessive inflammation, dental pulpitis, a mitochondrial disease or disorder, cardiovascular disease, stroke, disorders associated with stress, arthritis, osteoarthritis, preterm labor, a disorder that would benefit from decreased cellular glycolytic activity, muscle tissue damage associated with hypoxia or ischemia, a blood coagulation disorder, a fungal infection, ischemia, chronic pain associated with brain and/or spinal cord disease, hypertension, or any combination thereof.

PAX6 (also known as paired box protein Pax-6, aniridia type II protein (AN2) or oculorhombin), a transcription factor that has been highly conserved during evolution, is a key regulator of eye development in both vertebrates and invertebrates. During embryonic development, the PAX6 protein is thought to turn on (activate) genes involved in the formation of the eyes (Kroeber et al., 2010, Human Molecular Genetics, 19(17):3332-3342; Shaham et al., 2012, Progress in Retinal and Eye Research, 31(5):351-376; Swisa et al., Journal of Clinical Investigation, 127(1):230-243; Osumi et al., 2008, Stem Cells, 26(7):1663-1672), the brain and spinal cord (central nervous system), and the pancreas. After birth, continued PAX6 expression throughout life is critical to maintaining the proper phenotype of these cells and helping to avoid metaplastic responses following cellular injury. In humans, heterozygous mutations in PAX6 are causative for aniridia, a condition associated with a variety of ocular developmental anomalies including deficiency or hypoplasia of the iris, corneal opacities, foveal and optic nerve dysplasia and cataract. More rarely, mutations in PAX6 lead to Peters' anomaly, a condition that is characterized by a central corneal opacity (leukoma), a local absence of the corneal endothelium (to which the lens may adhere to) and iridocorneal adhesions. In mice with heterozygous mutations in Pax6, ocular defects are in general more extreme. In most cases, the eyes are less than half of their normal size (microphthalmos), the anterior chamber of the eye is missing, the retina is abnormally folded and the lens is absent or small and has anterior cataracts. About 50-75% of patients with aniridia develop an increase in intraocular pressure (TOP) in preadolescent or early adult years that commonly leads to optic nerve damage and glaucoma. TOP is generated via the aqueous humor circulation system. Aqueous humor is secreted by the ciliary processes into the posterior chamber of the eye and leaves the eye through the trabecular meshwork and Schlemm's canal, which are both localized at the iridocorneal angle of the anterior chamber. Studies in heterozygote Pax6-deficient mice, an animal model of aniridia, have identified defects in trabecular meshwork differentiation and the complete absence of Schlemm's canal. Similar structural defects may well account for the increase in TOP and the glaucoma phenotype, which are observed in humans with aniridia.

Cells in our body are constantly exposed to various stresses and threats to their genomic integrity (Li et al., 2015, Journal of Cellular Physiology, 230(10):2318-2327). The tumor suppressor protein p53 (also known as TP53) plays a critical role in successful defense against these threats by inducing apoptotic cell death or cell cycle arrest. p53 has also been shown to be critical for normal immune responses and modulation of inflammatory diseases. It also plays important roles in metabolism, stem cell maintenance, fertility, and the response to viral and other microbial infection (Munoz-Fontela et al., 2016, Nature Reviews Immunology, 16(12):741-750). In unstressed conditions, p53 levels and activity must be kept low to prevent lethal activation of apoptotic and senescence pathways (Haupt et al., 1997, Nature, 387(6630):296-299). However, upon DNA damage or other stressors, p53 is released from its inhibitory state to induce an array of innate immune, cell cycle, apoptosis, and other regulatory and transcription genes. The ubiquitin E3 ligase MDM2 (murine double minute 2 protein) is the most critical inhibitor of p53 that determines the cellular response to various p53-activating agents, including DNA damage. MDM2 activity is controlled by post-translational modifications such as phosphorylation. MDM2 activity can also be directly inhibited by small molecules that interfere with its interaction with p53 (Shangary and Wang, 2009, Annual Review of Pharmacology and Toxicology, 49:223-241) or by inhibiting its heterodimer formation with MDM4 (also known as MDMX) (Roxburgh et al., 2012, Carcinogenesis, 33(4):791-798). Deficiency of p53 is associated with susceptibility to cancer, impaired innate immunity, susceptibility to viral infection, impaired recovery from bacterial infection, impaired wound healing, increased cataract formation, vascular disease, and abnormal aging of tissues (Madenspacher et al., 2013, The Journal of Experimental Medicine, 210(5):891-904; Wiley et al., 2011, Disease Models & Mechanisms, 4(4):484-495; Tabas, 2001, Circulation Research, 88(8):747-749; Hirota et al., 2010, Journal of Clinical Investigation, 120(3):803-815).

5'-adenosine diphosphate ribose (ADPR) is a naturally occurring small molecule, which is also available commercially. Previous studies have shown that ADPR inhibits Sirt6 at concentrations between 10 to 1000 μM (Madsen et al., 2016, J. Biol. Chem., 291(13):7128-7141).

3 SUMMARY OF THE INVENTION

Provided herein are methods for treating, managing, or preventing an RNA virus-related disease or condition in a patient, said methods comprising administering to the patient an effective amount of 5'-adenosine diphosphate ribose (ADPR), or a pharmaceutically acceptable salt, solvate, hydrate, tautomer, stereoisomer, isotopologue, or polymorph thereof, or a pharmaceutical composition thereof, wherein the patient has or is at risk of developing an RNA virus-related disease or condition.

Provided herein are methods for treating, managing, or preventing a herpes virus-related disease or condition in a patient, said methods comprising administering to the patient an effective amount of ADPR, or a pharmaceutically acceptable salt, solvate, hydrate, tautomer, stereoisomer, isotopologue, or polymorph thereof, or a pharmaceutical composition thereof, wherein the patient has or is at risk of developing a herpes virus-related disease or condition.

Provided herein are methods for treating, managing, or preventing a disease or condition associated with sirtuin 6 (Sirt6) deficiency in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition associated with Sirt6 deficiency. In one embodiment, provided herein are methods for treating, managing, or preventing a disease or condition treatable, manageable, or preventable by increasing Sirt6 activity in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition treatable, manageable, or preventable by increasing Sirt6 activity. In one aspect, provided herein are methods of increasing the amount and/or the activity of Sirt6 in a patient in need thereof, comprising administering to the patient an effective amount of ADPR, or a pharmaceutically acceptable salt, solvate, hydrate, tautomer, stereoisomer, isotopologue, or polymorph thereof. In another aspect, provided herein are methods of increasing the activity of Sirt6 in a patient in need thereof, comprising administering to the patient an effective amount of ADPR, or a pharmaceutically acceptable salt, solvate, hydrate, tautomer, stereoisomer, isotopologue, or polymorph thereof.

Provided herein are methods for treating, managing, or preventing a disease or condition associated with Pax6 deficiency in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition associated with Pax6 deficiency. In one embodiment, provided herein are methods for treating, managing, or preventing a disease or condition treatable, manageable, or preventable by increasing Pax6 activity in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition treatable, manageable, or preventable by increasing Pax6 activity. In one aspect, provided herein are methods of increasing the amount and/or the activity of Pax6 in a patient in need thereof, comprising administering to the patient an effective amount of ADPR, or a pharmaceutically acceptable salt, solvate, hydrate, tautomer, stereoisomer, isotopologue, or polymorph thereof. In another aspect, provided herein are methods of increasing the activity of Pax6 in a patient in need thereof, comprising administering to the patient an effective amount of ADPR, or a pharmaceutically acceptable salt, solvate, hydrate, tautomer, stereoisomer, isotopologue, or polymorph thereof.

Provided herein are methods for treating, managing, or preventing a disease or condition associated with p53 deficiency in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition associated with p53 deficiency. In one embodiment, provided herein are methods for treating, managing, or preventing a disease or condition treatable, manageable, or preventable by increasing p53 activity in a patient, said methods comprising administering to the patient an effective amount of ADPR, or a pharmaceutically acceptable salt, solvate, hydrate, tautomer, stereoisomer, isotopologue, or polymorph thereof; wherein the patient has or is at risk of developing a disease or condition treatable, manageable, or preventable by increasing p53 activity. In one aspect, provided herein are methods of increasing the amount and/or the activity of p53 in a patient in need thereof, comprising administering to the patient an effective amount of ADPR, or a pharmaceutically acceptable salt, solvate, hydrate, tautomer, stereoisomer, isotopologue, or polymorph thereof. In another aspect, provided herein are methods of increasing the activity of p53 in a patient in need thereof, comprising administering to the patient an effective amount of ADPR, or a pharmaceutically acceptable salt, solvate, hydrate, tautomer, stereoisomer, isotopologue, or polymorph thereof.

In one embodiment, the RNA virus-related disease or condition is an HRSV-related disease or condition.

In certain embodiments, the RNA virus-related disease or condition (e.g., HRSV-related disease or condition) is a disease or condition that affects any portion of the eye, ear, mouth, upper respiratory tract, or lower respiratory tract. In one embodiment, the RNA virus-related disease or condition (e.g., HRSV-related disease or condition) is selected from, but not limited to, epi-bulbar disease, conjunctivitis, keratitis, kerato-conjunctivitis, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, exacerbation of emphysema, or exacerbation of a chronic lung disease.

In one embodiment, the herpes virus-related disease or condition is an HSV-1-related disease or condition.

In certain embodiments, the herpes virus-related disease or condition (e.g., HSV-1-related disease or condition) is a disease or condition that affects any portion of the eye, ear, mouth, upper respiratory tract, lower respiratory tract, genito-urinary system, skin, brain, liver, spleen, or nervous system. In one embodiment, the herpes virus-related disease or condition (e.g., HSV-1-related disease or condition) is selected from, but not limited to, epi-bulbar disease, conjunctivitis, keratitis, kerato-conjunctivitis, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, vaginitis, dermatitis, exacerbation of asthma, exacerbation of chronic obstructive pulmonary disease, exacerbation of emphysema, or exacerbation of a chronic lung disease.

In certain embodiments, the disease or condition associated with Sirt6 deficiency or the disease or condition treatable, manageable, or preventable by increasing Sirt6 activity is a viral disease, disease due to aging, diabetes mellitus, type 2 diabetes mellitus, respiratory disorder, chronic lung disease, chronic obstructive pulmonary disease, asthma, idiopathic pulmonary fibrosis, cystic fibrosis, ocular disorder, diabetic retinopathy, retinal disease, retinal detachment, adult macular degeneration, glaucoma, liver disease, non-alcoholic steatohepatitis, chronic hepatitis infection, neurodegenerative disorder (e.g., Alzheimer's disease), disorder resulting in cognitive decline, trauma resulting in brain or spinal cord injury, cancer, chemotherapy-induced neuropathy, neuropathy associated with an ischemic or traumatic event, an autoimmune disorder, disorder associated with excessive inflammation, dental pulpitis, mitochondrial disease or disorder, cardiovascular disease, stroke, disorder associated with stress, arthritis, osteoarthritis, preterm labor, disorder that would benefit from decreased cellular glycolytic activity, muscle tissue damage associated with hypoxia or ischemia, blood coagulation disorder, fungal infection, ischemia, chronic pain associated with brain and/or spinal cord disease, hypertension, or any combination thereof.

In certain embodiments, the disease or condition associated with Pax6 deficiency or the disease or condition treatable, manageable, or preventable by increasing Pax6 activity is aniridia, aniridia related eye disease, aniridia related keratopathy, keratoconus, uveitis, diabetic retinopathy, retinal disease, retinal detachment, acute retinal necrosis, Gillespie syndrome, Peters anomaly, WAGR syndrome, dry eye, presbyopia, myopia, glaucoma, congenital glaucoma, cataracts, corneal injury or infection, keratitis, keratoconjunctivitis, adult macular degeneration, diabetic retinopathy, post-operative recovery from eye or brain surgery, limbal stem cell deficiency, diabetes mellitus, type 2 diabetes mellitus, neurodegenerative disease (e.g., Alzheimer's disease, Parkinson's disease, and others), disorder resulting in cognitive decline, cerebellar ataxia, reduced olfaction, nystagmus, impaired auditory processing, impaired memory, autism, mental retardation, trauma resulting in brain or spinal cord injury, stroke, or any combination thereof.

In certain embodiments, the disease or condition associated with p53 deficiency or the disease or condition treatable, manageable, or preventable by increasing p53 activity is a viral disease, disease due to aging, diabetes mellitus, type 2 diabetes mellitus, respiratory disorder, chronic lung disease, chronic obstructive pulmonary disease, asthma, idiopathic pulmonary fibrosis, cystic fibrosis, ocular disorder, diabetic retinopathy, retinal disease, retinal detachment, adult macular degeneration, glaucoma, liver disease, non-alcoholic steatohepatitis, chronic hepatitis infection, neurodegenerative disorder (e.g., Alzheimer's disease, Parkinson's disease, and others), disorder resulting in cognitive decline, trauma resulting in brain or spinal cord injury, cancer, chemotherapy-induced neuropathy, neuropathy associated with an ischemic or traumatic event, an autoimmune disorder, disorder associated with excessive inflammation, dental pulpitis, mitochondrial disease or disorder, cardiovascular disease, stroke, disorder associated with stress, arthritis, osteoarthritis, preterm labor, disorder that would benefit from decreased cellular glycolytic activity, muscle tissue damage associated with hypoxia or ischemia, blood coagulation disorder, fungal infection, ischemia, chronic pain associated with brain and/or spinal cord disease, hypertension, or any combination thereof. In certain embodiments, the disease or condition associated with p53 deficiency or the disease or condition treatable, manageable, or preventable by increasing p53 activity is impaired wound healing, cataracts, presbyopia, or cancers secondary to viral infection.

In certain embodiments, ADPR, or a pharmaceutically acceptable salt, solvate, hydrate, tautomer, stereoisomer, isotopologue, or polymorph thereof, is administered by topical, oral, parenteral, mucosal, or inhalation route of administration. In one embodiment, ADPR as described herein is administered by inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear.

In certain embodiments, the methods provided herein comprise administering to the patient a pharmaceutical composition comprising ADPR, or a pharmaceutically acceptable salt, solvate, hydrate, tautomer, stereoisomer, isotopologue, or polymorph thereof, and an excipient, diluent, or carrier.

In a specific embodiment, the ADPR compound for use in the compositions and methods provided herein is in the form of its dilithium salt.

In certain embodiments, ADPR, or a pharmaceutically acceptable salt, solvate, hydrate, tautomer, stereoisomer, isotopologue, or polymorph thereof, is administered in combination with another medicament. In certain embodiments, the other medicament is an antiviral compound.

In one aspect, the methods provided herein comprise administering a pharmaceutical composition comprising (i) ADPR, or a solvate, hydrate, tautomer, stereoisomer, isotopologue, or polymorph thereof, and (ii) one or more pharmaceutically acceptable excipients, diluents or carriers; wherein the amount of ADPR in the pharmaceutical composition is in the range of about 0.001% w/w to about 10% w/w of the pharmaceutical composition. In certain embodiments, the pharmaceutical compositions comprise dilithium ADPR.

4 BRIEF DESCRIPTION OF THE FIGURES

FIG. 1 is a graph of luminescence vs. concentration of dilithium ADPR ($Li_2$-ADPR). The amount of luminescence directly quantitates the amount of HRSV replication in A549 cells. The results show a significant dose-dependent inhibition of HRSV replication with increasing concentrations of $Li_2$-ADPR. The pattern of inhibition was similar on days 1 and 2 following the initial infection on Day 0.

FIG. 2 is a graph of the percentage of A549 cells infected vs. the concentration of $Li_2$-ADPR. Cell infection was determined by the presence of green fluorescence in each cell. The data show that increasing concentrations of $Li_2$-ADPR results in a significant reduction in the percentage of cells infected on days 1 and 2 following the primary inoculation on day 0.

FIG. 3 is a graph of the percentage of primary human airway epithelial cells infected vs. the concentration of $Li_2$-ADPR. Cell infection was determined by the presence of luciferase activity. The data show that increasing concentrations of $Li_2$-ADPR results in a significant reduction in the percentage of cells infected on days 1 and 3 following the primary inoculation on day 0.

FIG. 4 depicts plate images from the plaque inhibition assay described in Example 4.

FIG. 5 shows the gel (a) and quantitative evaluation of Sirt6 deacetylation activity (b) in the presence of $Li_2$-ADPR. In this example, deacetylation activity is expressed as the inverse of H3K9Ac acetylation (as indicated by anti-H3K9Ac antibody) divided by the total H3 histone concentration. This was then converted to percent.

Figure 8:
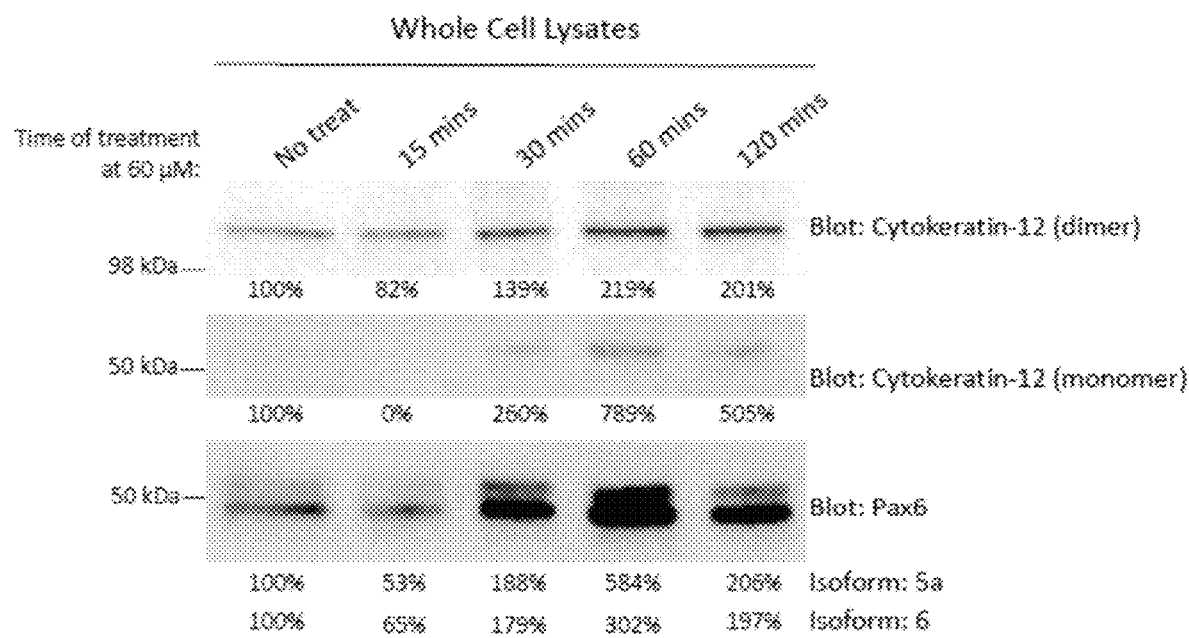

FIG. 8 shows the time dependent increase in protein concentration for Pax6 (isoforms 5a and 6) and cytokeratin 12 in human corneal epithelial cells incubated with $Li_2$-ADPR at 60 μM. All band intensities were calculated relative to "no treat."

Figure 9:
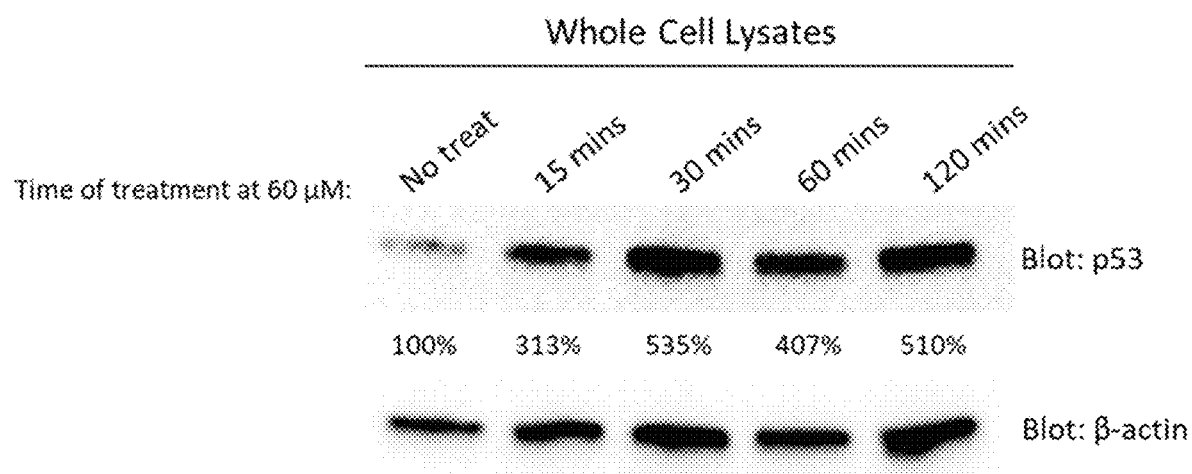

FIG. 9 shows the time dependent increase in protein concentration for p53 human corneal epithelial cells incubated $Li_2$-ADPR at 60 μM.

Figure 10:
Figure 10:
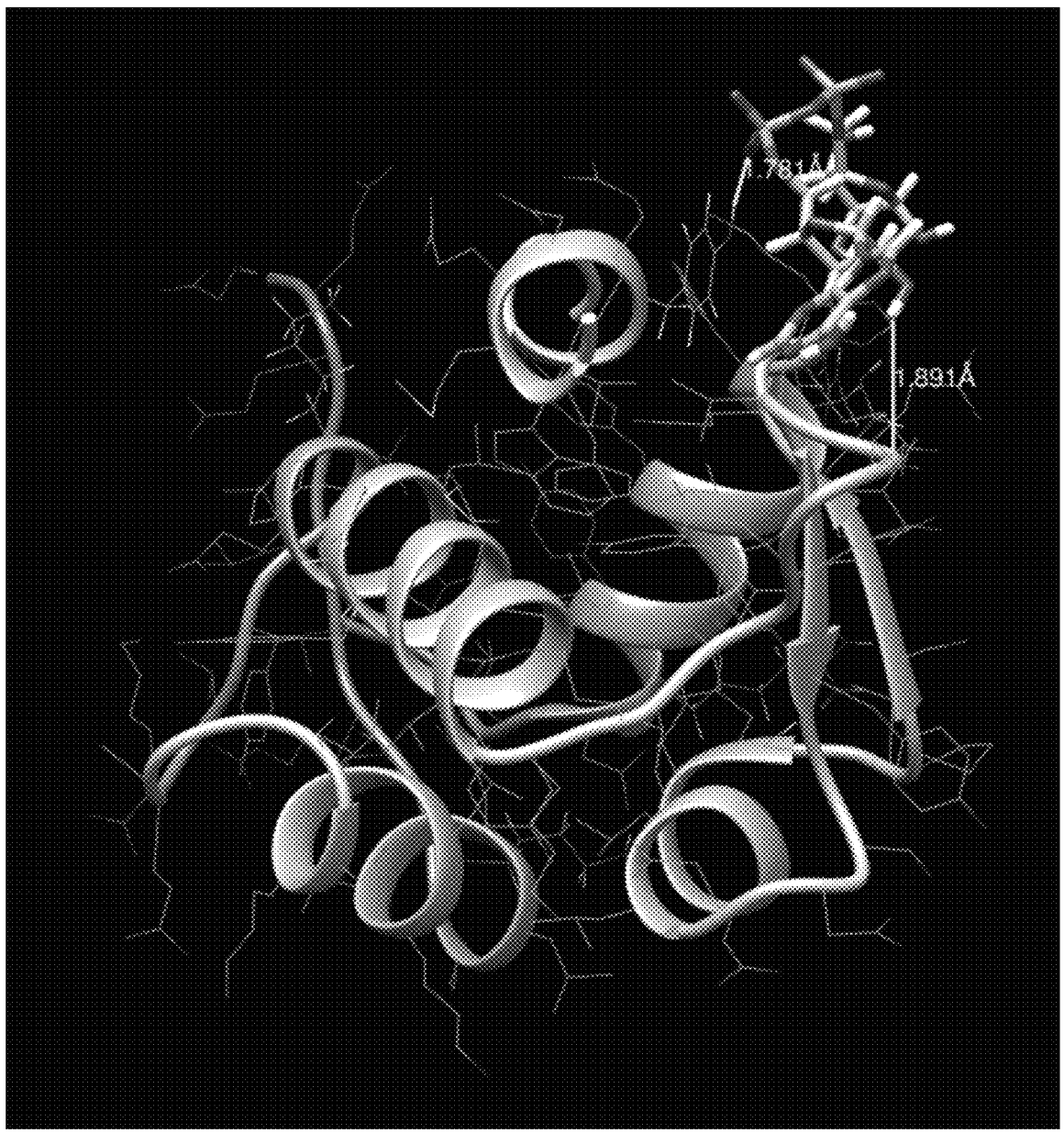

FIG. 10 shows an image of the in-silico docking of ADPR with MDM2 at the protein interface between MDM2 and MDM4 as a heterodimer (a) and at the protein binding interface between MDM2 and p53 (b).

Figure 11:
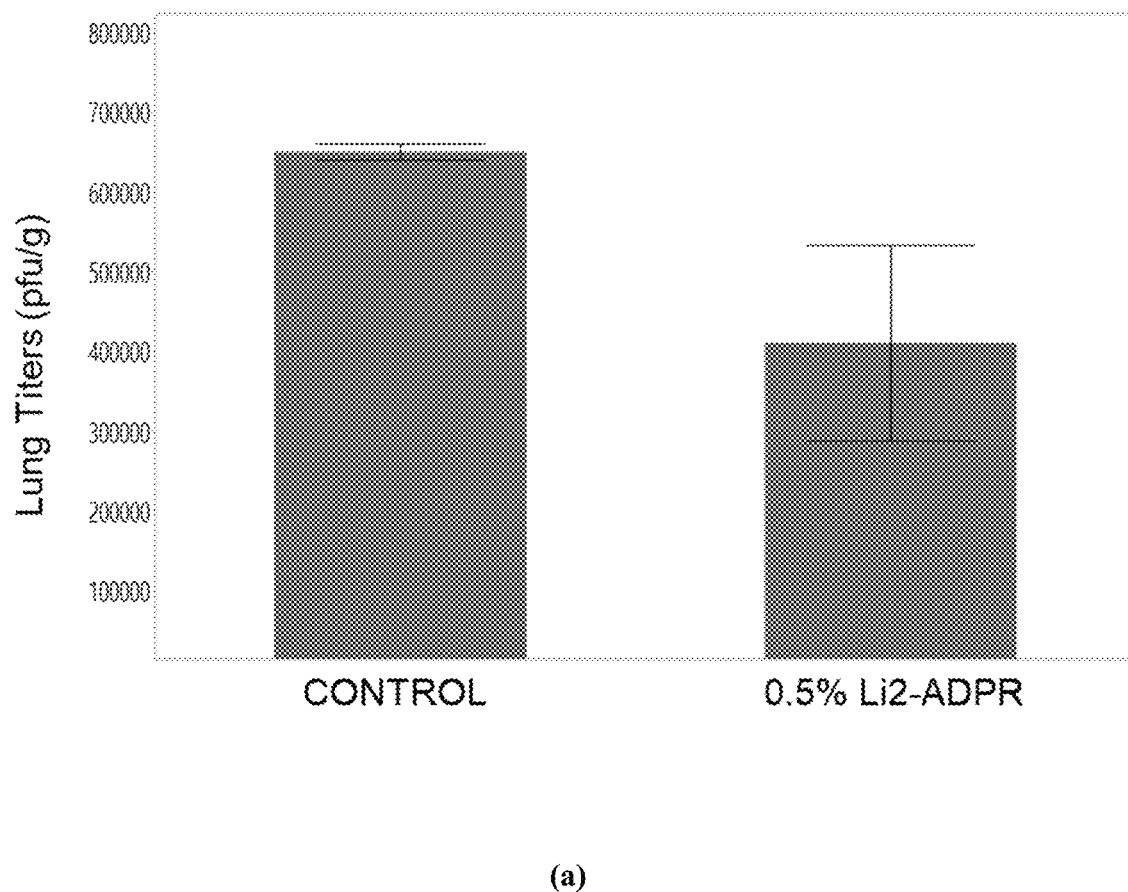
Figure 11:
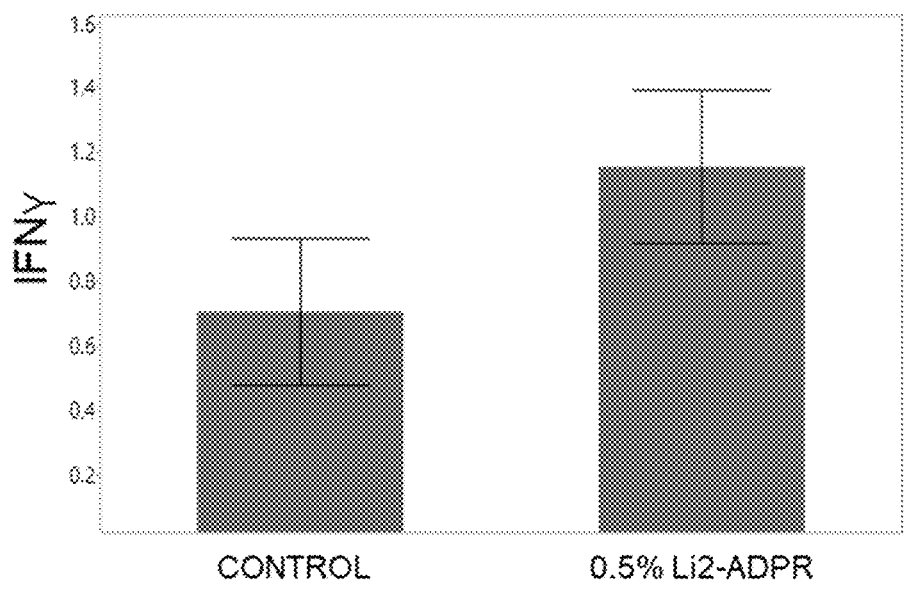
Figure 11:
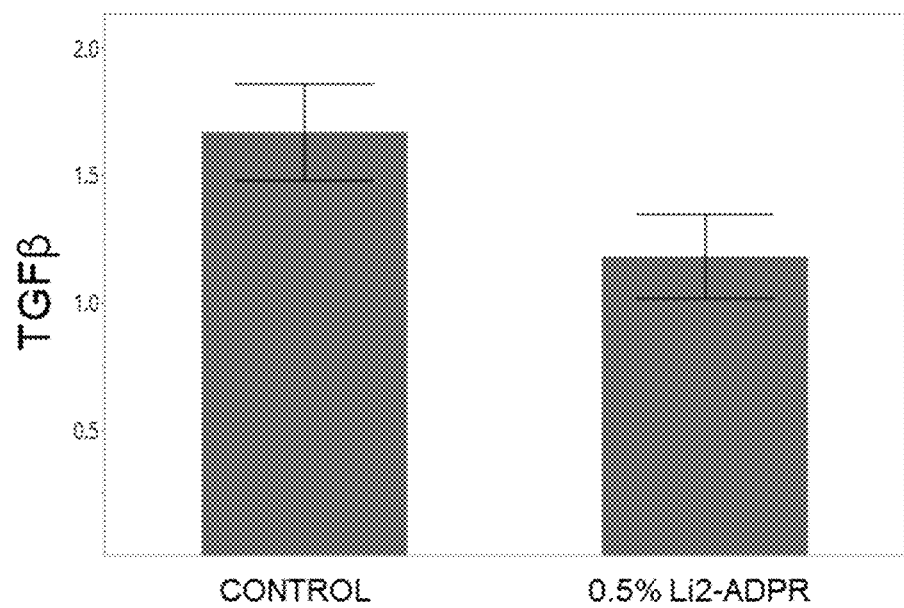

FIG. 11 shows results the results for lung tissue RSV titer (a), lung tissue interferon gamma (IFNγ) (b) and lung tissue transforming growth factor beta (TGFβ) (c). Each figure compares the results from control (phosphate buffered saline) and 0.5% $Li_2$-ADPR treated cotton rats. Tissue samples were obtained on Day 5 of treatment (50 microliters by nasal inhalation given 2 times per day) following infection with RSV.

Figure 12:
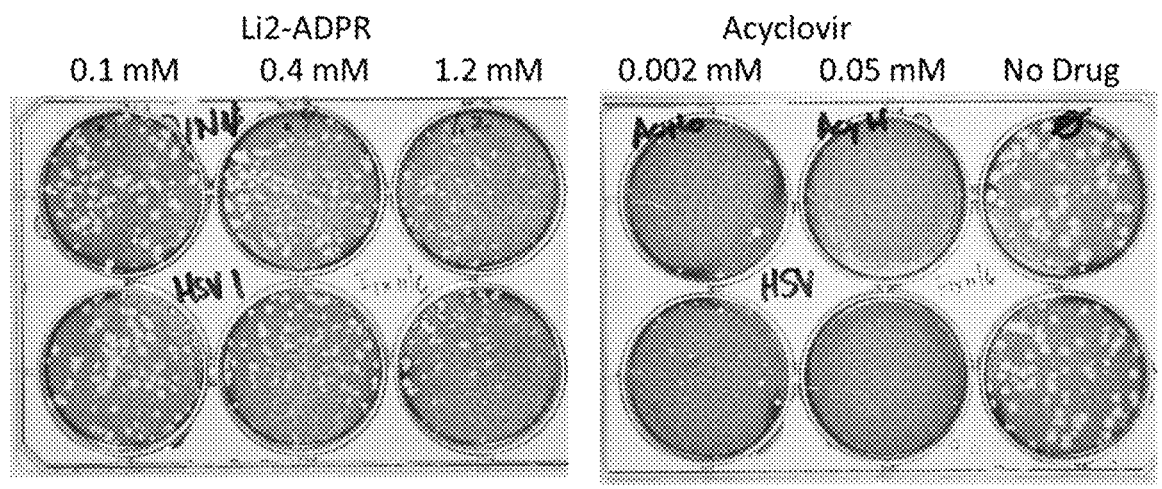

FIG. 12 shows the effect of $Li_2$-ADPR on plaque inhibition against HSV-1, performed in A549 cells.

5 DETAILED DESCRIPTION

5.1 Definitions

As used herein, the term "ADPR" is understood to include ADPR as well as a pharmaceutically acceptable salt, solvate, hydrate, tautomer, stereoisomer, isotopologue, or polymorph thereof.

As used herein, the term "dose(s)" means a quantity of ADPR, or a pharmaceutically acceptable salt, solvate, hydrate, tautomer, stereoisomer, isotopologue, or polymorph thereof, to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet).

As used herein, the term "daily dose" means a quantity of ADPR, or a pharmaceutically acceptable salt, solvate, hydrate, tautomer, stereoisomer, isotopologue, or polymorph thereof that is administered in a 24 hour period. Accordingly, a daily dose may be administered all at once (i.e., once daily dosing) or alternatively the daily dosing may be divided such that administration of ADPR, or a pharmaceutically acceptable salt, solvate, hydrate, tautomer, stereoisomer, isotopologue, or polymorph thereof, is twice daily, three times daily, four times daily, five times daily, six times daily, or even continuously throughout the day.

As used herein, the term "patient" or "subject" include animals, such as mammals, including, but not limited to, primates (e.g., humans), cows, sheep, goats, horses, dogs, cats, rabbits, rats, mice, monkeys, chickens, turkeys, quails, or guinea pigs and the like. In one embodiment, as used herein, the term "patient" or "subject" means a mammal. In one embodiment, as used herein, the term "patient" or "subject" means a human.

As used herein, an "effective amount" refers to that amount of ADPR, or a pharmaceutically acceptable salt, solvate, hydrate, tautomer, stereoisomer, isotopologue, or polymorph thereof that is sufficient to provide a therapeutic benefit in the treatment of the disease or to delay or minimize symptoms associated with the disease. In certain embodiments, the disease is an RNA virus-related disease or condition. In certain embodiments, the disease is an HRSV-related disease or condition. In certain embodiments, the disease is a herpes virus related disease or condition (e.g. herpes simplex virus-1 (HSV-1) related disease or condition). In certain embodiments, the disease is a disease or condition associated with Sirt6 deficiency or a disease or condition treatable, manageable, or preventable by increasing Sirt6 activity. In certain embodiments, the disease is a disease or condition associated with Pax6 deficiency or a disease or condition treatable, manageable, or preventable by increasing Pax6 activity. In certain embodiments, the disease is a disease or condition associated with p53 deficiency or a disease or condition treatable, manageable, or preventable by increasing p53 activity.

As used herein, the terms "prevent", "preventing" and "prevention" are art-recognized, and when used in relation to a condition, such as an RNA virus-related disease or condition, an HRSV-related disease or condition, a herpes virus-related disease or condition, an HSV-1-related disease or condition, a disease or condition associated with Sirt6 deficiency, or a disease or condition treatable, manageable, or preventable by increasing Sirt6 activity, a disease or condition associated with Pax6 deficiency, or a disease or condition treatable, manageable, or preventable by increasing Pax6 activity, a disease or condition associated with p53 deficiency, or a disease or condition treatable, manageable, or preventable by increasing p53 activity, is well understood in the art, and includes administration of a compound which reduces the frequency of, or delays the onset of, symptoms of a medical condition in a patient relative to a patient who does not receive the composition.

As used herein, the terms "treat", "treating" and "treatment" refer to the reversing, reducing, or arresting the symptoms, clinical signs, and underlying pathology of a condition in manner to improve or stabilize a patient's condition. The terms "treat" and "treatment" also refer to the eradication or amelioration of the disease or symptoms associated with the disease. In certain embodiments, such terms refer to minimizing the spread or worsening of the disease resulting from the administration of a compound as disclosed herein to a patient with such a disease. In certain embodiments, the disease is an RNA virus-related disease or condition. In certain embodiments the disease is an HRSV-related disease or condition. In certain embodiments, the disease is a herpes virus-related disease or condition. In certain embodiments, the disease is an HSV-1-related disease or condition. In certain embodiments, the disease is a disease or condition associated with Sirt6 deficiency or a disease or condition treatable, manageable, or preventable by increasing Sirt6 activity. In certain embodiments, the disease is a disease or condition associated with Pax6 deficiency or a disease or condition treatable, manageable, or preventable by increasing Pax6 activity. In certain embodiments, the disease is a disease or condition associated with p53 deficiency or a disease or condition treatable, manageable, or preventable by increasing p53 activity.

As used herein, the terms "manage", "managing" and "management" encompasses preventing the recurrence of the particular disease or condition in a patient who had suffered from it, reducing mortality rates of the patients, and/or maintaining a reduction in severity or avoidance of a symptom associated with the disease or condition being managed.

As used herein, the term "pharmaceutical composition" refers to compositions suitable for use or prescribed treatment in treating, managing, or preventing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency or a disease or condition treatable, manageable, or preventable by increasing p53 activity.

As used herein, the term "pharmaceutically acceptable salt" refers to those salts that are, within the scope of sound medical judgment, suitable for use in contact with the human tissue without undue toxicity, irritation, allergic response and the like and are commensurate with a reasonable benefit/risk ratio.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 15%, 10%, 9%, 8%, 7%, 6%, 5%, 4%, 3%, 2%, 1%, 0.5%, 0.05%, or 0.005% of a given value or range.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present invention can comprise, consist of, or consist essentially of the essential elements and limitations of the invention described herein, as well as any additional or optional ingredients, components, or limitations described herein or otherwise useful in compositions and methods of the general type as described herein.

5.2 5'-Adenosine Diphosphate Ribose (ADPR)

The uses and compositions provided herein relate to 5'-adenosine diphosphate ribose (ADPR; ADP-ribose; adenosine 5'-(trihydrogen diphosphate),P'→5-ester with D-ribose; adenosine 5'-(trihydrogen pyrophosphate),5'→5-ester with D-ribofuranose; adenosine 5'-diphosphate, D-ribose ester; adenosine 5'-pyrophosphate, 5'→5-ester with D-ribofuranose; ribofuranose, 5-(adenosine 5'-pyrphosphoryl)-D-ribose; adenosine 5'-diphosphoribose; adenosine diphosphate ribose; adenosine diphosphoribose; adenosine pyrophosphate-ribose; ribose adenosinediphosphate).

ADPR is a naturally occurring small molecule well known in the chemical literature. It is often characterized by the general formula $C_{15}H_{23}N_5O_{14}P_2$, and includes, for example, various salts such as sodium salt corresponding to the following general structure of formula (I):

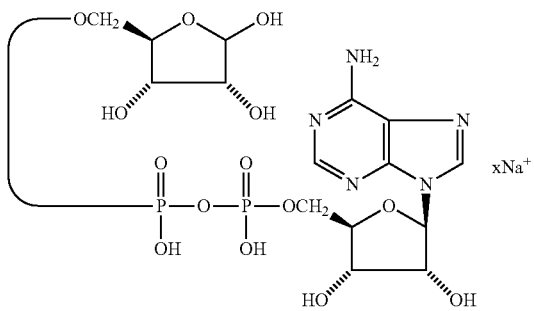

ADPR can be readily prepared by methods well known in the chemical arts. It is also commercially available as a purified raw material, an example of which can be purchased from Sigma or Sigma-Aldrich Co.

The ADPR compound can also include those derivatives in which basic nitrogen-containing groups are quaternized with materials such as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; aryl alkyl halides like benzyl and phenethyl bromides and many others.

Examples of acids which may be employed to form pharmaceutically acceptable acid addition salts of ADPR include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of the ADPR by reacting an acidic moiety with a suitable base such as, but not limited to, the hydroxide, carbonate or bicarbonate of a pharmaceutically acceptable metal ion or with ammonia or an organic primary, secondary or tertiary amine. Non-limiting examples of pharmaceutically acceptable salts include those based on alkali metals, alkaline earth metals, transition metals, or post-transition metals, such as lithium (including dilithium), sodium (including disodium), potassium, calcium, magnesium, aluminum, zinc, cobalt, and copper salts and the like, and nontoxic quaternary ammonia and amine captions including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine, and the like.

In one embodiment, the ADPR compound for use in the compositions and methods provided herein is synthesized via the hydrolysis of nicotinamide adenine dinucleotide (NAD+) in the presence of an alkaline base, such as, but not limited to, lithium hydroxide or sodium hydroxide. In such an embodiment, the ADPR thus synthesized is isolated in the form of its mono or di salt of the metal ion of the corresponding base.

In a specific embodiment, the ADPR compound for use in the compositions and methods provided herein is in the form of its sodium salt. In one embodiment, the ADPR compound is in the form of its monosodium salt. In another embodiment, the ADPR compound is in the form of its disodium salt.

In another specific embodiment, the ADPR compound for use in the compositions and methods provided herein is in the form of its lithium salt. In one embodiment, the ADPR compound is in the form of its monolithium salt. In another embodiment, the ADPR compound is in the form of its dilithium salt. In one embodiment, the ADPR compound is in the form of a combination of one or more of sodium, lithium, potassium, calcium, magnesium, zinc, cobalt, and/or copper salts.

5.3 Methods of Treatment, Management and Prevention

Provided herein are methods for treating, managing or preventing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity, comprising administering ADPR or a pharmaceutically acceptable salt, solvate, hydrate, tautomer, stereoisomer, isotopologue, or polymorph thereof, or a pharmaceutical composition thereof, to a patient having or at risk of developing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity.

In certain embodiments, provided herein are methods for treating or preventing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity, comprising administering to a patient having or at risk of developing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity an effective amount of ADPR, or a pharmaceutically acceptable salt, solvate, hydrate, tautomer, stereoisomer, isotopologue, or polymorph thereof, or a pharmaceutical composition thereof.

In certain embodiments, provided herein are methods for treating, managing, or preventing an RNA virus-related disease or condition (e.g., HRSV-related disease or condition) in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the RNA virus-related disease or condition (e.g., HRSV-related disease or condition).

In certain embodiments, provided herein are methods for treating, managing, or preventing an RNA virus-related disease or condition (e.g., HRSV-related disease or condition) in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the RNA virus-related disease or condition (e.g., HRSV-related disease or condition).

In certain embodiments, the RNA virus-related disease or condition includes, but is not limited to, asthma or chronic obstructive pulmonary disease.

In certain embodiments, the RNA virus-related disease or condition is caused by an RNA virus, wherein the RNA virus is a Coronaviridae family virus, a Pneumoviridae family virus, a Paramyxoviridae family virus, a Picornaviridae family virus, or a Orthomyxoviridae family virus. In certain embodiments, the Coronaviridae family virus is Coronavirus or SARS, the Pneumoviridae family virus is human respiratory syncytial virus (HRSV), the Paramyxoviridae family virus is human parainfluenza virus, measles virus or mumps virus, the Picornaviridae family virus is rhinovirus, and the Orthomyxoviridae family virus is influenza virus. In certain embodiments, the RNA virus is a Pneumoviridae family virus. In one embodiment, the RNA virus is HRSV.

In certain embodiments, provided herein are methods for treating, managing or preventing an RNA virus-related disease or condition (e.g., HRSV-related disease or condition), comprising administering to a patient having an RNA virus-related disease or condition (e.g., HRSV-related disease or condition), or to a patient at risk of developing an RNA virus-related disease or condition (e.g., HRSV-related disease or condition), an effective amount of ADPR, or a pharmaceutically acceptable salt, solvate, hydrate, tautomer, stereoisomer, isotopologue, or polymorph thereof, wherein the RNA virus-related disease or condition (e.g., HRSV-related disease or condition) is a disease or condition that affects any portion of the eye, ear, mouth, upper respiratory tract, or lower respiratory tract. In some embodiments, the RNA virus-related disease or condition (e.g., HRSV-related disease or condition) is selected from, but not limited to, epi-bulbar disease, conjunctivitis, keratitis, kerato-conjunctivitis, corneal abrasion, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, exacerbation of emphysema, or exacerbation of a chronic lung disease. In certain embodiments, the RNA virus-related disease or condition (e.g., HRSV-related disease or condition) is conjunctivitis, keratitis, kerato-conjunctivitis, pharyngitis, tonsillitis, laryngitis, rhinitis, sinusitis, bronchitis, bronchiolitis, or pneumonia. In one embodiment, the RNA virus-related disease or condition (e.g., HRSV-related disease or condition) is bronchitis, bronchiolitis, or pneumonia. In another embodiment, the RNA virus-related disease or condition (e.g., HRSV-related disease or condition) is pharyngitis, tonsillitis, sinusitis, or laryngitis. In another embodiment, the RNA virus-related disease or condition (e.g., HRSV-related disease or condition) is keratitis, conjunctivitis, or keratoconjunctivitis. In some embodiments, the RNA virus-related disease or condition is HRSV-related disease or condition.

In certain embodiments, provided herein are methods for treating, managing or preventing a herpes virus related disease or condition (e.g. HSV-1 related disease or condition) in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the herpes virus related disease or condition (e.g. HSV-1 related disease or condition).

In certain embodiments, provided herein are methods for treating, managing, or preventing a herpes virus related disease or condition (e.g. HSV-1 related disease or condition) in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the herpes virus related disease or condition (e.g. HSV-1 related disease or condition).

In certain embodiments, the herpes virus related disease or condition includes, but is not limited to, asthma or chronic obstructive pulmonary disease.

In certain embodiments, the herpes virus-related disease or condition is a disease or condition that affects the eye, skin, genito-urinary tract, vagina, nerves, nervous system, brain, liver, spleen, pharynx, tonsils, or other tissue described herein.

In certain embodiments, provided herein are methods for treating, managing, or preventing a disease or condition associated with Sirt6 deficiency in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition associated with Sirt6 deficiency.

In certain embodiments, provided herein are methods for treating, managing, or preventing a disease or condition associated with Sirt6 deficiency in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition associated with Sirt6 deficiency.

In certain embodiments, provided herein are methods for treating, managing, or preventing a disease or condition treatable, manageable, or preventable by increasing Sirt6 activity in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing Sirt6 activity. In one embodiment, the methods provided herein comprise increasing Sirt6 deacetylation activity. In another embodiment, the methods provided herein comprise increasing Sirt6 deacetylation of Histone 3 activity. In another embodiment, the methods provided herein comprise increasing Sirt6 deacetylation of a lysine residue of Histone 3 activity. In another embodiment, the methods provided herein comprise increasing Sirt6 deacetylation of lysine 9 (K9) of Histone 3 activity.

In certain embodiments, provided herein are methods for treating, managing, or preventing a disease or condition treatable, manageable, or preventable by increasing Sirt6 activity in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing Sirt6 activity.

In certain embodiments, the disease or condition associated with Sirt6 deficiency or the disease or condition treatable, manageable, or preventable by increasing Sirt6 activity includes, but is not limited to, asthma or chronic obstructive pulmonary disease.

In certain embodiments, the disease or condition associated with Sirt6 deficiency or the disease or condition treatable, manageable, or preventable by increasing Sirt6 activity is a viral disease, disease due to aging, diabetes mellitus, type 2 diabetes mellitus, respiratory disorder, chronic lung disease, chronic obstructive pulmonary disease, asthma, idiopathic pulmonary fibrosis, cystic fibrosis, ocular disorder, diabetic retinopathy, retinal disease, retinal detachment, adult macular degeneration, glaucoma, liver disease, non-alcoholic steatohepatitis, chronic hepatitis infection, neurodegenerative disorder (e.g., Alzheimer's disease), disorder resulting in cognitive decline, trauma resulting in brain or spinal cord injury, cancer, chemotherapy-induced neuropathy, neuropathy associated with an ischemic or traumatic event, an autoimmune disorder, disorder associated with excessive inflammation, dental pulpitis, mitochondrial disease or disorder, cardiovascular disease, stroke, disorder associated with stress, arthritis, osteoarthritis, preterm labor, disorder that would benefit from decreased cellular glycolytic activity, muscle tissue damage associated with hypoxia or ischemia, blood coagulation disorder, fungal infection, ischemia, chronic pain associated with brain and/or spinal cord disease, hypertension, or any combination thereof.

In certain embodiments, provided herein are methods of increasing the amount and/or the activity of Sirt6 in a patient in need thereof, comprising administering to the patient an effective amount of ADPR, or a pharmaceutically acceptable salt, solvate, hydrate, tautomer, stereoisomer, isotopologue, or polymorph thereof. In certain embodiments, provided herein are methods of increasing the activity of Sirt6 in a patient in need thereof, comprising administering to the patient an effective amount of ADPR, or a pharmaceutically acceptable salt, solvate, hydrate, tautomer, stereoisomer, isotopologue, or polymorph thereof.

In certain embodiments, provided herein are methods for treating, managing, or preventing a disease or condition associated with Pax6 deficiency in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition associated with Pax6 deficiency.

In certain embodiments, provided herein are methods for treating, managing, or preventing a disease or condition associated with Pax6 deficiency in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition associated with Pax6 deficiency.

In certain embodiments, provided herein are methods for treating, managing, or preventing a disease or condition treatable, manageable, or preventable by increasing Pax6 activity in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing Pax6 activity.

In certain embodiments, provided herein are methods for treating, managing, or preventing a disease or condition treatable, manageable, or preventable by increasing Pax6 activity in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing Pax6 activity.

In certain embodiments, the disease or condition associated with Pax6 deficiency or the disease or condition treatable, manageable, or preventable by increasing Pax6 activity includes, but is not limited to, diseases of the eye, brain, and pancreas.

In certain embodiments, the disease or condition associated with Pax6 deficiency or the disease or condition treatable, manageable, or preventable by increasing Pax6 activity is aniridia, aniridia related eye disease, aniridia related keratopathy, keratoconus, uveitis, diabetic retinopathy, retinal disease, retinal detachment, acute retinal necrosis, Gillespie syndrome, Peters anomaly, WAGR syndrome, dry eye, presbyopia, myopia, glaucoma, congenital glaucoma, cataracts, corneal injury or infection, keratitis, keratoconjunctivitis, adult macular degeneration, diabetic retinopathy, post-operative recovery from eye or brain surgery, limbal stem cell deficiency, diabetes mellitus, type 2 diabetes mellitus, neurodegenerative disease (e.g., Alzheimer's disease, Parkinson's disease, and others), disorder resulting in cognitive decline, cerebellar ataxia, reduced olfaction, nystagmus, impaired auditory processing, impaired memory, autism, mental retardation, trauma resulting in brain or spinal cord injury, stroke, or any combination thereof.

In certain embodiments, provided herein are methods of increasing the amount and/or the activity of Pax6 in a patient in need thereof, comprising administering to the patient an effective amount of ADPR, or a pharmaceutically acceptable salt, solvate, hydrate, tautomer, stereoisomer, isotopologue, or polymorph thereof. In certain embodiments, provided herein are methods of increasing the activity of Pax6 in a patient in need thereof, comprising administering to the patient an effective amount of ADPR, or a pharmaceutically acceptable salt, solvate, hydrate, tautomer, stereoisomer, isotopologue, or polymorph thereof.

In certain embodiments, provided herein are methods for treating, managing, or preventing a disease or condition associated with p53 deficiency in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition associated with p53 deficiency.

In certain embodiments, provided herein are methods for treating, managing, or preventing a disease or condition associated with p53 deficiency in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition associated with p53 deficiency.

In certain embodiments, provided herein are methods for treating, managing, or preventing a disease or condition treatable, manageable, or preventable by increasing p53 activity in a patient, said method comprising administering to the patient an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing p53 activity. In one embodiment, the methods provided herein comprise increasing p53 protein concentration by inhibiting MDM2.

In certain embodiments, provided herein are methods for treating, managing, or preventing a disease or condition treatable, manageable, or preventable by increasing p53 activity in a patient, said method comprising administering to the patient a pharmaceutical composition comprising an effective amount of ADPR, or a pharmaceutically acceptable salt, solvate, hydrate, tautomer, stereoisomer, isotopologue, or polymorph thereof, wherein the patient is having or at risk of developing the disease or condition treatable, manageable, or preventable by increasing p53 activity.

In certain embodiments, the disease or condition associated with p53 deficiency or the disease or condition treatable, manageable, or preventable by increasing p53 activity is a viral disease, disease due to aging, diabetes mellitus, type 2 diabetes mellitus, respiratory disorder, chronic lung disease, chronic obstructive pulmonary disease, asthma, idiopathic pulmonary fibrosis, cystic fibrosis, ocular disorder, diabetic retinopathy, retinal disease, retinal detachment, adult macular degeneration, glaucoma, cataracts, presbyopia, liver disease, non-alcoholic steatohepatitis, chronic hepatitis infection, neurodegenerative disorder (e.g., Alzheimer's disease, Parkinson's disease), disorder resulting in cognitive decline, trauma resulting in brain or spinal cord injury, cancer, cancer secondary to viral infection, chemotherapy-induced neuropathy, neuropathy associated with an ischemic or traumatic event, an autoimmune disorder, disorder associated with excessive inflammation, dental pulpitis, mitochondrial disease or disorder, cardiovascular disease, stroke, disorder associated with stress, arthritis, osteoarthritis, preterm labor, disorder that would benefit from decreased cellular glycolytic activity, muscle tissue damage associated with hypoxia or ischemia, blood coagulation disorder, fungal infection, ischemia, chronic pain associated with brain and/or spinal cord disease, hypertension, impaired wound healing, or any combination thereof.

In certain embodiments, provided herein are methods of increasing the amount and/or the activity of p53 in a patient in need thereof, comprising administering to the patient an effective amount of ADPR, or a pharmaceutically acceptable salt, solvate, hydrate, tautomer, stereoisomer, isotopologue, or polymorph thereof. In certain embodiments, provided herein are methods of increasing the activity of p53 in a patient in need thereof, comprising administering to the patient an effective amount of ADPR, or a pharmaceutically acceptable salt, solvate, hydrate, tautomer, stereoisomer, isotopologue, or polymorph thereof.

In certain embodiments, provided herein are methods for treating, managing or preventing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity, comprising administering to a patient having, or at risk of developing, an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity, an effective amount of ADPR, or a pharmaceutically acceptable salt, solvate, hydrate, tautomer, stereoisomer, isotopologue, or polymorph thereof, wherein the ADPR compound is administered by topical, oral, parenteral, mucosal, or inhalation route of administration. In one embodiment, ADPR as described herein is administered by inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear.

In one embodiment, the RNA virus-related disease or condition (e.g., HRSV-related disease or condition) is a respiratory disorder or a viral infection of at least one tissue of the respiratory tract, including, but not limited to, the eye, ear, nose, mouth, nasal pharynx, oropharynx, pharynx, larynx, trachea, bronchi, bronchioles, lungs, and alveoli.

In one embodiment, the herpes virus related disease or condition (e.g. HSV-1 related disease or condition) is a respiratory disorder or a viral infection of at least one tissue of the respiratory tract, including, but not limited to, the eye, ear, nose, mouth, nasal pharynx, oropharynx, pharynx, larynx, trachea, bronchi, bronchioles, lungs, and alveoli.

In one embodiment, the disease or condition associated with Sirt6 deficiency or the disease or condition treatable, manageable, or preventable by increasing Sirt6 activity is a respiratory disorder or a viral infection of at least one tissue of the respiratory tract, including, but not limited to, the eye, ear, nose, mouth, nasal pharynx, oropharynx, pharynx, larynx, trachea, bronchi, bronchioles, lungs, and alveoli.

In one embodiment, provided herein are methods for treating, managing, or preventing an infection in a patient exposed to an RNA virus. In one embodiment, provided herein are methods for treating, managing, or preventing an infection in a patient exposed to an HRSV infection. In a specific embodiment, the ADPR is in the form of its dilithium salt.

In one embodiment, the RNA virus-related disease or condition (e.g., HRSV-related disease or condition) is an eye disorder. In certain embodiments, the eye disorder is a microorganism infection of at least one tissue of the eye, conjunctivitis, keratitis, kerato-conjunctivitis, corneal abrasion, ulcerative infectious keratitis, epithelial keratitis, stromal keratitis, uveitis, acute glaucoma, or blepharitis. In a specific embodiment, the eye disorder is infectious keratoconjunctivitis.

In one embodiment, the herpes virus related disease or condition (e.g. HSV-1 related disease or condition) is an eye disorder. In certain embodiments, the eye disorder is a microorganism infection of at least one tissue of the eye, conjunctivitis, keratitis, kerato-conjunctivitis, corneal abrasion, ulcerative infectious keratitis, epithelial keratitis, stromal keratitis, uveitis, acute glaucoma, or blepharitis. In a specific embodiment, the eye disorder is infectious keratoconjunctivitis.

In one embodiment, the disease or condition associated with Sirt6 deficiency or the disease or condition treatable, manageable, or preventable by increasing Sirt6 activity is an eye disorder. In certain embodiments, the eye disorder is a microorganism infection of at least one tissue of the eye, conjunctivitis, keratitis, kerato-conjunctivitis, corneal abrasion, ulcerative infectious keratitis, epithelial keratitis, stromal keratitis, uveitis, acute glaucoma, or blepharitis. In a specific embodiment, the eye disorder is infectious keratoconjunctivitis.

In one embodiment, the RNA virus-related disease or condition (e.g., HRSV-related disease or condition) is caused by inflammation. In a specific embodiment, the RNA virus-related disease or condition (e.g., HRSV-related disease or condition) is caused by inflammation of the cornea and/or conjunctiva. In a specific embodiment, the RNA virus-related disease or condition is caused by inflammation of the lung. In a specific embodiment, the ADPR is in the form of its dilithium salt.

In one embodiment, the herpes virus related disease or condition (e.g. HSV-1 related disease or condition) is caused by inflammation. In a specific embodiment, the herpes virus related disease or condition (e.g. HSV-1 related disease or condition) is caused by inflammation of the cornea and/or conjunctiva. In a specific embodiment, the ADPR is in the form of its dilithium salt.

In one embodiment, the disease or condition associated with Sirt6 deficiency or the disease or condition treatable, manageable, or preventable by increasing Sirt6 activity is caused by inflammation. In a specific embodiment, the disease or condition associated with Sirt6 deficiency or the disease or condition treatable, manageable, or preventable by increasing Sirt6 activity is caused by inflammation of the cornea and/or conjunctiva. In a specific embodiment, the ADPR is in the form of its dilithium salt.

In one embodiment, the disease or condition associated with Pax6 deficiency or the disease or condition treatable, manageable, or preventable by increasing Pax6 activity is caused by inflammation. In a specific embodiment, the disease or condition associated with Sirt6 deficiency or the disease or condition treatable, manageable, or preventable by increasing Sirt6 activity is caused by inflammation of the cornea and/or conjunctiva. In a specific embodiment, the ADPR is in the form of its dilithium salt.

In one embodiment, the disease or condition associated with p53 deficiency or the disease or condition treatable, manageable, or preventable by increasing p53 activity is caused by inflammation. In a specific embodiment, the disease or condition associated with p53 deficiency or the disease or condition treatable, manageable, or preventable by increasing p53 activity is caused by inflammation of the cornea and/or conjunctiva. In a specific embodiment, the ADPR is in the form of its dilithium salt.

In one embodiment, the administering step comprises administering ADPR and a metal salt, wherein the total amount of ADPR and the metal salt is in the range of about 0.001 mg to about 5 mg per dose. In one embodiment, each dose is between 10 microliters to 200 microliters. In another embodiment, each dose is between 20 microliters to 80 microliters.

In one embodiment, the administering step comprises administering the pharmaceutical composition in the form of a solution. In one embodiment, the solution is administered to the eye one to eight times a day. In one embodiment, the solution is administered to the eye one to twenty-four times a day.

In one embodiment, the method further comprises the step of storing the composition for at least one month, at least three months, at least six months, or at least 1 year before the administering step.

5.4 Combination Therapy

In certain embodiments, ADPR or a pharmaceutically acceptable salt, solvate, hydrate, tautomer, stereoisomer, isotopologue, or polymorph thereof, or a pharmaceutical composition thereof, may be administered in combination with another medicament. Such combination therapy may be achieved by way of the simultaneous, sequential, or separate dosing of the individual components of the treatment. Additionally, when administered as a component of such combination therapy, ADPR as disclosed herein, and the other medicament may be synergistic, such that the daily dose of either or both of the components may be reduced as compared to the dose of either component that would normally be given as a monotherapy. Alternatively, when administered as a component of such combination therapy, ADPR as disclosed herein and the other medicament may be additive, such that the daily dose of each of the components is similar or the same as the dose of either component that would normally be given as a monotherapy.

In certain embodiments, the other medicament is an antiviral compound or a metal salt. In some embodiments, the other medicament is an antiviral compound. In some embodiments, the other medicament is Abacavir, Acyclovir (Aciclovir), Adefovir, Amantadine, Amprenavir, Ampligen, Arbidol, Atazanavir, Balavir, Cidofovir, Dolutegravir, Darunavir, Delavirdine, Didanosine, Docosanol, Edoxudine, Efavirenz, Elvitegravir, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Norvir, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, or Zidovudine. In some embodiments, the other medicament is Ribavirin, Cidofovir, Acyclovir, or Ganciclovir. In a specific embodiment, the other medicament is Ribavirin.

In certain embodiments, the other medicament is a lithium, zinc, cobalt, or copper salt. In certain embodiments, the other medicament is lithium benzoate, lithium bromide, lithium chloride, lithium sulfate, lithium tetraborate, lithium acetate, zinc chloride, zinc sulfate, zinc bromide, cobalt chloride, cobalt bromide, copper bromide ($CuBr_2$), copper chloride ($CuCl_2$), or copper sulfate. In a specific embodiment, the other medicament is lithium chloride.

5.5 Doses and Dosing Regimens

In certain embodiments, the RNA virus-related disease or condition (e.g., HRSV-related disease or condition), the herpes virus related disease or condition (e.g. HSV-1 related disease or condition), the disease or condition associated with Sirt6 deficiency, the disease or condition treatable, manageable, or preventable by increasing Sirt6 activity, the disease or condition associated with Pax6 deficiency, the disease or condition treatable, manageable, or preventable by increasing Pax6 activity, the disease or condition associated with p53 deficiency, or the disease or condition treatable, manageable, or preventable by increasing p53 activity, can be treated by administering to a patient having, or at risk of developing, the disease or condition as described herein from about 0.0001 mg/kg to about 1000 mg/kg, about 0.001 mg/kg to about 100 mg/kg, about 0.1 mg/kg to about 10 mg/kg or about 0.1 mg/kg to about 5.0 mg/kg of ADPR, or a pharmaceutically acceptable salt, solvate, hydrate, tautomer, stereoisomer, isotopologue, or polymorph thereof.

In certain embodiments, the pharmaceutical composition may comprise from about 0.00001 to 100% such as from 0.001 to 10% or from 0.01% to 2% by weight of ADPR, or a pharmaceutically acceptable salt, solvate, hydrate, tautomer, stereoisomer, isotopologue, or polymorph thereof.

In certain embodiments, the RNA virus-related disease or condition (e.g., HRSV-related disease or condition), the herpes virus related disease or condition (e.g. HSV-1 related disease or condition), the disease or condition associated with Sirt6 deficiency, the disease or condition treatable, manageable, or preventable by increasing Sirt6 activity, the disease or condition associated with Pax6 deficiency, the disease or condition treatable, manageable, or preventable by increasing Pax6 activity, the disease or condition associated with p53 deficiency, or the disease or condition treatable, manageable, or preventable by increasing p53 activity, can be treated by administering to a patient having, or at risk of developing, the disease or condition as described herein an amount of about 0.005 mg to about 1000 mg, about 0.01 mg to about 100 mg, about 0.01 mg to about 10 mg, about 0.01 mg to about 1 mg, about 0.01 mg to about 0.1 mg, about 0.1 mg to about 10 mg, about 0.1 mg to about 5.0 mg, 0.1 mg to about 1 mg of ADPR, or a pharmaceutically acceptable salt, solvate, hydrate, tautomer, stereoisomer, isotopologue, or polymorph thereof. In one embodiment, the concentration of ADPR, or a pharmaceutically acceptable salt, solvate, hydrate, tautomer, stereoisomer, isotopologue, or polymorph thereof is in the range of about 0.05 mg/mL to about 30 mg/mL. In another embodiment, the concentration of ADPR, or a pharmaceutically acceptable salt, solvate, hydrate, tautomer, stereoisomer, isotopologue, or polymorph thereof is in the range of about 1 mg/mL to about 20 mg/mL.

In certain such embodiments, ADPR as described herein is administered by topical, oral, parenteral, mucosal, or inhalation route of administration. In one embodiment, ADPR as described herein is administered by inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, nebulization, spray, oral delivery, intra-tracheal infusion, intra-bronchial, or infusion to a surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface. In one embodiment, the exterior cellular or tissue surface includes, but is not limited to, the surface of the skin, eye, nail, hair, or ear. In a specific embodiment, ADPR as described herein is administered topically in a concentration ranging from about 0.05 mg/mL to about 30 mg/mL. In another embodiment, ADPR as described herein is administered topically in a concentration ranging from about 1 mg/mL to about 20 mg/mL. In some embodiments, the administering is done by intravenous, intra-arterial, or intraductal infusion In certain embodiments, the RNA virus-related disease or condition (e.g., HRSV-related disease or condition), the herpes virus related disease or condition (e.g. HSV-1 related disease or condition), the disease or condition associated with Sirt6 deficiency, or the disease or condition treatable, manageable, or preventable by increasing Sirt6 activity, can be treated by administering to a patient having or at risk of developing a disease or condition as described herein a daily dose of about 0.005 mg to about 1000 mg, about 0.01 mg to about 100 mg, about 0.01 mg to about 10 mg, about 0.01 mg to about 1 mg, about 0.01 mg to about 0.1 mg, about 0.1 mg to about 10 mg, about 0.1 mg to about 5.0 mg, 0.1 mg to about 1 mg of ADPR, or a pharmaceutically acceptable salt, solvate, hydrate, tautomer, stereoisomer, isotopologue, or polymorph thereof. In one embodiment, the concentration of ADPR, or a pharmaceutically acceptable salt, solvate, hydrate, tautomer, stereoisomer, isotopologue, or polymorph thereof is in the range of about 0.05 mg/mL to about 30 mg/mL. In another embodiment, the concentration of ADPR, or a pharmaceutically acceptable salt, solvate, hydrate, tautomer, stereoisomer, isotopologue, or polymorph thereof is in the range of about 1 mg/mL to about 20 mg/mL. In certain such embodiments, ADPR as described herein is administered by topical, oral, parenteral, mucosal, or inhalation route of administration. In one embodiment, ADPR as described herein is administered by inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear. In a specific embodiment, ADPR as described herein is administered topically in a concentration ranging from about 0.05 mg/mL to about 30 mg/mL. In another embodiment, ADPR as described herein is administered topically in a concentration ranging from about 1 mg/mL to about 20 mg/mL.

The suitability of ADPR, or a pharmaceutically acceptable salt, solvate, hydrate, tautomer, stereoisomer, isotopologue, or polymorph thereof, for the treatment, management, or prevention of an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with p53 deficiency, or a disease or condition treatable, manageable, or preventable by increasing p53 activity, can be confirmed by using the assays described herein. For example, infection with an RNA virus (e.g., HRSV) or herpes virus (e.g. HSV-1) can be diagnosed by a viral culture, an antigen detection test, or by a polymerase chain reaction test.

5.6 Pharmaceutical Compositions

Provided herein are pharmaceutical compositions comprising ADPR or a pharmaceutically acceptable salt, solvate, hydrate, tautomer, stereoisomer, isotopologue, or polymorph thereof, effective for treating, managing, or preventing an RNA virus-related disease or condition (e.g., HRSV-related disease or condition), a herpes virus related disease or condition (e.g. HSV-1 related disease or condition), a disease or condition associated with Sirt6 deficiency, a disease or condition treatable, manageable, or preventable by increasing Sirt6 activity, a disease or condition associated with Pax6 deficiency, a disease or condition treatable, manageable, or preventable by increasing Pax6 activity, a disease or condition associated with p53 deficiency, or a disease or condition treatable, manageable, or preventable by increasing p53 activity.

In some embodiments, the pharmaceutical composition is effective for treating or preventing a HRSV-related disease or condition. In some embodiments, the pharmaceutical composition is effective for treating or preventing a HSV-1-related disease or condition. In some embodiments, the pharmaceutical composition is effective for treating or preventing a disease or condition associated with Sirt6 deficiency or a disease or condition treatable, manageable, or preventable by increasing Sirt6 activity. In some embodiments, the pharmaceutical composition is effective for treating or preventing a disease or condition associated with Pax6 deficiency, or a disease or condition treatable, manageable, or preventable by increasing Pax6 activity. In some embodiments, the pharmaceutical composition is effective for treating or preventing a disease or condition associated with p53 deficiency, or a disease or condition treatable, manageable, or preventable by increasing p53 activity.

Pharmaceutical compositions may be used in the preparation of individual, single unit dosage forms. Pharmaceutical compositions and dosage forms of the present invention comprise ADPR, or a pharmaceutically acceptable salt, solvate, hydrate, tautomer, stereoisomer, isotopologue, or polymorph thereof. The pharmaceutical compositions and dosage forms of the present invention can be prepared by any known or otherwise effective method for formulating or manufacturing the selected product form. For example, ADPR, or a pharmaceutically acceptable salt, solvate, hydrate, tautomer, stereoisomer, isotopologue, or polymorph thereof, can be formulated along with common excipients, diluents, or carriers, and formed into tablets, capsules, solutions, suspensions, emulsions, microemulsions, nanoemulsions, syrups, elixirs, sprays, powders, aerosols (e.g., dry powder aerosols, liquid aerosols), dissolving media (e.g., rapid dissolving tablet, film, strip), suppositories, ointments, or any other suitable dosage form. In a specific embodiment, the pharmaceutical composition is in the form of a solution.

Non-limiting examples of suitable excipients, diluents, and carriers include: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

Like the amounts and types of excipients, the amount and specific type of the active ingredient (e.g., ADPR as disclosed herein) in a dosage form may differ depending on factors including, but not limited to, the route by which it is to be administered to patients. In certain embodiments, administration of the pharmaceutical composition or dosage form comprising ADPR, or a pharmaceutically acceptable salt, solvate, hydrate, tautomer, stereoisomer, isotopologue, or polymorph thereof, may be by topical, oral, parenteral, mucosal, or inhalation route. As used herein, the term "parenteral" includes intravitreous, intraocular, intracorneal, subcutaneous, intradermal, intravascular injections, such as intravenous, intra-arterial, intramuscular, intraluminal and any another similar injection or infusion technique. In certain embodiments, ADPR, or a pharmaceutically acceptable salt, solvate, hydrate, tautomer, stereoisomer, isotopologue, or polymorph thereof, may be administered orally, such as in a tablet, capsule, or liquid formulation. In certain embodiments, ADPR, or a pharmaceutically acceptable salt, solvate, hydrate, tautomer, stereoisomer, isotopologue, or polymorph thereof, may be administered topically. In certain embodiments, ADPR, or a pharmaceutically acceptable salt, solvate, hydrate, tautomer, stereoisomer, isotopologue, or polymorph thereof, may be administered intranasally or by inhalation.

Topical administration as described herein includes applying an effective amount of ADPR, or a pharmaceutically acceptable salt, solvate, hydrate, tautomer, stereoisomer, isotopologue, or polymorph thereof, to any mucosal and/or epithelial surface of the body including that associated with, but not limited to, the skin, eyes, ears, nose, sinuses, mouth, lips, pharynx, larynx, epiglottis, trachea, bronchi, bronchioles, alveoli, esophagus, stomach, intestines, colon, rectum, anus, vagina, cervix, and any other portions of the dermatologic, gastrointestinal, respiratory, and/or genitourinary tracts.

Additionally, ADPR, or a pharmaceutically acceptable salt, solvate, hydrate, tautomer, stereoisomer, isotopologue, or polymorph thereof, can also be formulated as a sustained or prolonged release dosage forms including a dosage form that releases the active ingredient only or preferably in a particular part of the intestinal tract, preferably over an extended or prolonged period of time to further enhance effectiveness. In one embodiment, ADPR as described herein is formulated as a sustained or prolonged release dosage form including a dosage form that releases the active ingredient only or preferably in a particular part of the respiratory tract, preferably over an extended or prolonged period of time to further enhance effectiveness. The coatings, envelopes, and protective matrices in such a dosage form may be made, for example, from polymeric substances or waxes well known in the pharmaceutical arts.

In one embodiment, provided herein are pharmaceutical compositions comprising ADPR, wherein the amount of ADPR in the pharmaceutical composition is in the range of about 0.0001% w/w to about 100% w/w of the pharmaceutical composition. In one embodiment, the amount of ADPR in the pharmaceutical composition is in the range of about 0.0001% w/w to about 90% w/w, about 0.0001% w/w to about 80% w/w, about 0.0001% w/w to about 70% w/w, about 0.0001% w/w to about 60% w/w, about 0.0001% w/w to about 50% w/w, about 0.0001% w/w to about 40% w/w, about 0.0001% w/w to about 30% w/w, about 0.0001% w/w to about 20% w/w, or about 0.0001% w/w to about 10% w/w of the pharmaceutical composition.

In one embodiment, provided herein are pharmaceutical compositions comprising ADPR, wherein the amount of ADPR in the pharmaceutical composition is in the range of about 0.001% w/w to about 10% w/w of the pharmaceutical composition. In one embodiment, the amount of ADPR in the pharmaceutical composition is in the range of about 0.001% w/w to about 7% w/w, about 0.001% w/w to about 5% w/w, about 0.001% w/w to about 3% w/w, about 0.001% w/w to about 1% w/w, about 0.001% w/w to about 0.5% w/w, about 0.001% w/w to about 0.1% w/w, about 0.001% w/w to about 0.05% w/w, about 0.001% w/w to about 0.01% w/w, about 0.001% w/w to about 0.005% w/w, about 0.005% w/w to about 10% w/w, about 0.005% w/w to about 7% w/w, about 0.005% w/w to about 5% w/w, about 0.005% w/w to about 3% w/w, about 0.005% w/w to about 1% w/w, about 0.005% w/w to about 0.5% w/w, about 0.005% w/w to about 0.1% w/w, about 0.005% w/w to about 0.05% w/w, about 0.005% w/w to about 0.01% w/w, about 0.01% w/w to about 10% w/w, about 0.01% w/w to about 7% w/w, about 0.01% w/w to about 5% w/w, about 0.01% w/w to about 3% w/w, about 0.01% w/w to about 1% w/w, about 0.01% w/w to about 0.5% w/w, about 0.01% w/w to about 0.1% w/w, about 0.01% w/w to about 0.05% w/w, about 0.05% w/w to about 10% w/w, about 0.05% w/w to about 7% w/w, about 0.05% w/w to about 5% w/w, about 0.05% w/w to about 3% w/w, about 0.05% w/w to about 1% w/w, about 0.05% w/w to about 0.5% w/w, about 0.05% w/w to about 0.1% w/w, about 0.1% w/w to about 10% w/w, about 0.1% w/w to about 7% w/w, about 0.1% w/w to about 5% w/w, about 0.1% w/w to about 3% w/w, about 0.1% w/w to about 1% w/w, about 0.1% w/w to about 0.5% w/w, about 0.5% w/w to about 10% w/w, about 0.5% w/w to about 7% w/w, about 0.5% w/w to about 5% w/w, about 0.5% w/w to about 3% w/w, about 0.5% w/w to about 1% w/w, about 1% w/w to about 10% w/w, about 1% w/w to about 7% w/w, about 1% w/w to about 5% w/w, about 1% w/w to about 3% w/w, about 3% w/w to about 10% w/w, about 3% w/w to about 7% w/w, about 3% w/w to about 5% w/w, about 5% w/w to about 10% w/w, about 5% w/w to about 7% w/w, or about 7% w/w to about 10% w/w of the pharmaceutical composition.

In one embodiment, the amount of ADPR in the pharmaceutical composition is in the range of about 0.01% w/w to about 10% w/w of the pharmaceutical composition. In one embodiment, the amount of ADPR in the pharmaceutical composition is in the range of about 0.1% w/w to about 2.5% w/w of the pharmaceutical composition. In another embodiment, the amount of ADPR in the pharmaceutical composition is in the range of about 0.5% w/w to about 2% w/w of the pharmaceutical composition.

In certain embodiments, the pharmaceutical composition provided herein comprises (i) dilithium ADPR, or a solvate, hydrate, tautomer, stereoisomer, isotopologue, or polymorph thereof, and (ii) one or more pharmaceutically acceptable excipients; wherein the amount of dilithium ADPR in the pharmaceutical composition is in the range of about 0.001% w/w to about 10% w/w of the pharmaceutical composition.

In one embodiment, provided herein is a pharmaceutical composition suitable for topical administration to the eye, respiratory tract, and/or gastrointestinal tract effective for treatment and/or prophylaxis of a RNA virus or herpes virus infection or a disorder associated with a Sirt6 deficiency of at least one tissue of the eye, respiratory tract, and/or gastrointestinal tract, wherein the pharmaceutical composition comprises ADPR, wherein the amount of ADPR is in the range of about 0.001% w/w to about 10% w/w of the pharmaceutical composition.

In one embodiment, the prophylaxis is prophylaxis of infection following corneal abrasion or ocular surgery.

In one embodiment, the pharmaceutical composition is suitable for administration to the eye. In a specific embodiment, the pharmaceutical composition suitable for administration to the eye further comprises a topical anesthetic which relieves pain. In one embodiment, the topical anesthetic is proparacaine, lidocaine, tetracaine or combinations thereof.

In one embodiment, the pharmaceutical composition further comprises a penetration enhancer which enhances the penetration of ADPR into the tissues of the eye, respiratory tract, vagina, cervix, skin, or gastrointestinal tract. In a specific embodiment, the penetration enhancer is a topical anesthetic.

In one embodiment, the pharmaceutical composition further comprises an antimicrobial preservative. In one embodiment, the antimicrobial preservative is sodium tetraborate, boric acid, benzalkonium chloride, thimerosal, chlorobutanol, methyl paraben, propyl paraben, phenylethyl alcohol, EDTA, sorbic acid, Onamer M or combinations thereof. In one embodiment, the amount of antimicrobial preservative in the pharmaceutical composition is in the range of about 0.001% w/w to about 1.0% w/w by weight of the pharmaceutical composition. In a specific embodiment, the pharmaceutical composition is in the form of a solution.

In one embodiment, the pharmaceutical composition further comprises a cosolvent/surfactant. In one embodiment, the cosolvent/surfactant is polysorbate 20, polysorbate 60, polysorbate 80, Pluronic F68, Pluronic F84, Pluronic P103, cyclodextrin, tyloxapol or combinations thereof. In one embodiment, the amount of the cosolvent/surfactant in the pharmaceutical composition is in the range of about 0.01% w/w to about 2% w/w of the pharmaceutical composition.

In one embodiment, the pharmaceutical composition further comprises one or more viscosity increasing agents. In one embodiment, the viscosity increasing agent is polyvinyl alcohol, polyvinyl pyrrolidone, methyl cellulose, hydroxy propyl methylcellulose, hydroxyethyl cellulose, carboxymethyl cellulose, hydroxy propyl cellulose, polyethylene glycol, or combinations thereof. In one embodiment, the amount of the viscosity increasing agent in the pharmaceutical composition is in the range of about 0.01% w/w to about 2% w/w of the pharmaceutical composition. In a specific embodiment, the pharmaceutical composition is in the form of a solution.

In one embodiment, the pharmaceutical composition is in the form of a solution, suspension, emulsion, ointment, cream, gel, or a controlled release/sustained release formulation. In one embodiment, the pharmaceutical composition is in the form of a solution, suspension, suspension, emulsion, microemulsion, nanoemulsion, syrup, elixir, dry powder, aerosol, liquid aerosol, tablet, or dissolving media. In one embodiment, the dissolving media is a rapid dissolving tablet, film or strip. In one embodiment, the pharmaceutical composition is in the form of an aqueous solution.

5.6.1 Topical Ocular Formulations

In certain embodiments, a pharmaceutical formulation described in above may be specifically adjusted for topical application to the eye. In certain specific embodiments, disclosed herein are pharmaceutical formulations comprising ADPR as described herein as topical ophthalmic solutions or suspensions (eye drops), which are normally available as a sterile, isotonic (i.e., a pH of between about 3 and about 8, between about 4 to about 8, between about 7 to about 8, or about 7.4) solution, optionally further comprising a preservative and/or a viscosity enhancer.

The term "eye drops" as used herein refers to a pharmaceutical liquid formulation which is administered in the form of drops on the external surface of the eye and which has a local effect on the posterior segment of the eye, including the choroids, retinal pigment epithelium, retina, macula, fovea, optic nerve and vitreous humor.

Accordingly, in certain embodiments, a pharmaceutical formulation provided herein comprising ADPR as described herein, may be formulated with purified water and adjusted for physiological pH and isotonicity. Examples of buffering agents to maintain or adjust pH include, but are not limited to, acetate buffers, citrate buffers, phosphate buffers and borate buffers. Examples of tonicity adjustors are sodium chloride, mannitol and glycerin.

The eye drop formulation is then optionally aliquoted into either a plurality of discrete, sterile disposable cartridges each of which is suitable for unit dosing, or a single cartridge for unit dosing. Such a single disposable cartridge may be, for example, a conical or cylindrical specific volume dispenser, with a container having side-walls squeezable in a radial direction to a longitudinal axis in order to dispense the container contents therefrom at one end of the container. Such disposable containers can be used to dispense eye drops at 0.3 to 0.4 mL per unit dosing, and are ideally adaptable for the delivery of eye drops.

Ophthalmic eye-drop solutions or suspensions may also be packaged in multi-dose form, for example, as a plastic bottle with an eye-dropper. In such formulations, preservatives are optionally added to prevent microbial contamination after opening of the container. Suitable preservatives include, but are not limited to: sodium tetraborate, boric acid, benzalkonium chloride, thimerosal, chlorobutanol, methylparaben, propylparaben, phenylethyl alcohol, edetate disodium, sorbic acid, polyquaternium-1, or other agents known to those skilled in the art, and all of which are contemplated for use in the present invention. Preservative-containing formulations may comprise from about 0.001 to about 1.0% weight/volume of the preservative.

In certain embodiments, polymers may be added to ophthalmic solutions or suspensions in order to increase the viscosity of the vehicle, thereby prolonging contact of the solution or suspension with the cornea and enhancing bioavailability. In certain embodiments, such polymers are selected from cellulose derivatives (e.g., methylcellulose, hydroxyethylcellulose, hydroxypropylcellulose or carboxymethylcellulose), dextran 70, gelatin, polyols, glycerin, polyethylene glycol 300, polyethylene glycol 400, polysorbate 80, propylene glycol, polyvinyl alcohol and povidone, or a combination thereof.

In certain embodiments ophthalmic solutions or suspensions as disclosed herein may further comprise stabilizer/solubilizer such as a cyclodextrin. In certain such embodiments, the cyclodextrin is selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin.

In certain embodiments, a pharmaceutical formulation as disclosed herein, such as a pharmaceutical formulation comprising ADPR as described herein, may be administered in a sustained release ophthalmic solution or suspension formulation.

In certain embodiments, a pharmaceutical formulation as disclosed herein, such as a pharmaceutical formulation comprising ADPR as described herein, may be formulated for administration through an ocular drug delivery system, such as, but not limited to, a colloidal dosage form, such as nanoparticles, nanomicelles, liposomes, microemulsions, bioadhesive gels and fibrin sealant-based approaches to sustain drug levels at the target site. Other ocular drug delivery systems include drug-eluting contact lenses, ultrasound-mediated drug delivery, ocular iontophoresis, and drug-coated microneedles.

In certain embodiments, the frequency of administration can vary greatly. Depending on the needs of each subject and the severity of the disease to be treated, such administration may occur once every 6 months, once every 5 months, once every 4 months, once every 3 months, once every 2 months, once a month, once every 3 weeks, once every 2 weeks, once a week, once every 6 days, once every 5 days once every 4 days once every 3 days, once every 2 days, or once a day.

In certain embodiments, the frequency of administration can vary greatly, depending on the needs of each subject and the severity of the disease to be treated, such administration may be from about once a week to about ten times a day, such as from about three times a week to about three times a day, or once or twice a day.

5.6.2 Formulations for Intranasal Administration or by Inhalation

In certain embodiments, the pharmaceutical composition provided herein is administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

5.6.3 Oral Formulations

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic colloidal silicon dioxide product sold by Cabot Co. of Boston, Mass.), and mixtures thereof. If used at all, glidants may be used in an amount of less than about 1 weight percent of the pharmaceutical compositions or dosage forms into which they are incorporated.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

6 EXAMPLES

6.1 Example 1. Inhibition of HRSV Replication by Li$_2$-ADPR in A549 Cells

Drug Preparation and Handling: Li$_2$-ADPR, 250 mg, in one glass vial, was received as a powder and stored at −20° C. in the dark until use. On the day of the experiment, Li$_2$-ADPR was solubilized to 250 mg/ml using 1 ml of autoclaved, distilled, and deionized water. Solubilized Li$_2$-ADPR was further diluted to target concentrations of 2.7 mg/ml, 0.9 mg/ml, 0.3 mg/ml, and 0.1 mg/ml in virus growth media (DMEM, 2.5% Fetal Bovine Serum and antibiotic).

Inoculation and Treatment: 250 pfu (plaque-forming unit) of RSV encoding a *Renilla* Luciferase reporter gene was used to inoculate A549 cells in a 96-well plate for 2 hours at 37° C. Afterwards, the inoculum was replaced with 200 µl of fresh virus growth medium containing the target concentrations of Li$_2$-ADPR described above and incubated at 37° C. Fresh media containing the same target drug concentrations were added to remaining samples each day. At 24 and 48 hours post infection, cells were lysed and assayed for luciferase, as described by the manufacturer (*Renilla* Luciferase Assay System; Promega). Samples were transferred to a 96-well solid black plate and luminescence was quantified using a PE Wallac Victor 2 1420-012 system microplate reader. Assays were performed in triplicate. Data was plotted using GraphPad Prism software.

Conclusion: Li$_2$-ADPR was capable of inhibiting RSV replication in A549 cells. The effects were dose-dependent with the greatest inhibition of RSV replication observed when the highest concentration of drug (2.7 mg/ml; ~five-fold difference) was used. Inhibition of RSV replication was also observed at the lowest concentration of drug (0.1 mg/ml; ~two-fold difference).

6.2 Example 2. Reduction of HRSV Cellular Infection by Li$_2$-ADPR in A549 Cells Images: 250 pfu (plaque-forming unit) of RSV encoding a Green Fluorescent Protein reporter gene was used to inoculate A549 cells in a 96-well plate, as for Example 1 (above). Images were taken every day at the same time points as above. Bright field and fluorescence images were taken at 10× magnifications using an EVOS fl AMG digital inverted microscope. Infected cells were counted.

Conclusion: Li$_2$-ADPR significantly reduced the percentage of A549 cells infected with HRSV. The effects were dose-dependent with the greatest reduction of HRSV infection observed when the highest concentration of drug (2.7 mg/ml; ~85% reduction) was used. Inhibition of HRSV replication was also observed at the lowest concentration of drug (0.1 mg/ml; ~50% reduction).

6.3 Example 3. Reduction of HRSV Cellular Infection by Li$_2$-ADPR in Primary Human Airway Epithelial Cells Drug Preparation and Handling: Li$_2$-ADPR, 250 mg, in one glass vial, was received as a powder and stored at −20° C. in the dark until use. Li$_2$-ADPR was solubilized to 250 mg/ml using 1 ml of autoclaved, distilled, and deionized water. Solubilized Li$_2$-ADPR was further diluted to target concentrations of 2.7 mg/ml and 0.9 mg/ml in virus growth media (DMEM, 2.5% Fetal Bovine Serum and antibiotic).

Inoculation and Treatment: 250 pfu (plaque-forming unit) of RSV encoding a *Renilla* Luciferase reporter gene was used to inoculate the apical surface of human airway epithelial (HAE) cultures for 2 hours at 37° C. Afterwards, the inoculum was removed and 500 µl of fresh HAE growth media containing the indicated concentrations of $Li_2$-ADPR was added to the basolateral surface of the cultures. Cultures were incubated at 37° C. Fresh media containing the target drug concentrations were added to the cultures each day. Data was plotted using GraphPad Prism software.

Virus Replication/Spread Assay: At 24 and 72 hours post inoculation, cultures were lysed and assayed for luciferase activity as described by the manufacturer (*Renilla* Luciferase Assay System; Promega). They were then transferred to a 96-well solid black plate and luminescence was quantified using a PE Wallac Victor 2 1420-012 system microplate reader. Assays were performed in triplicate.

Conclusion: $Li_2$-ADPR was capable of significantly inhibiting RSV replication in HAE cultures. The effects were dose-dependent with the greatest inhibition of RSV replication observed when the highest concentration of drug (2.7 mg/ml) was used.

6.4 Example 4. Effect of ADPR (Sodium Salt) on Plaque Inhibition Against Herpes Simplex Virus Type 1 (HSV-1), Strain KOS Background: Adenosine 5'-diphosphoribose Sodium Salt, Sigma A0752-100 mg, Lot SLBJ4805V, in one 100 mg vial ("Sample") was solubilized to concentration 120 mg/ml in water for irrigation. Herpesvirus plaque inhibition assay were set up on the same day. The remainder of the solubilized Sample was placed in dark at 4° C. until use.

Dilutions: Sample solution was diluted 1:40 in virus growth media for the first Sample dilution of 3 mg/ml. Five additional step dilutions were made in the specific virus growth medium to generate 1 mg/ml, 300 µg/ml, 100 µg/ml, 30 µg/ml, and 10 µg/ml, and 6-well plates labeled per Table 1.

TABLE 1

Sample Labeling

| Sample Label on plate photographs | Sample Concentration |
|---|---|
| 1PR (HSV) | 3 mg/ml |
| 2PR (HSV) | 1 mg/ml |
| 3PR (HSV) | 300 µg/ml |
| 4PR (HSV) | 100 µg/ml |
| 5PR (HSV) | 30 µg/ml |
| 6PR (HSV) | 10 µg/ml |

Approach: Vero cells were plated at $1 \times 10^5$ per $cm^2$ in 6-well plates. After 18 hours growth media was removed from each prepared cell well and 1 ml of each Sample dilution was added. After incubating one hour at 37° C., approximately 60 plaque forming units HSV-1 strain KOS were added per well. Virus was permitted to adsorb to the cells for two hours and then the media was aspirated from the monolayers and replaced with herpes growth media containing Sample dilutions per Table 1, and agarose. After incubating three days at 37° C., monolayers were fixed, agarose removed, stained with crystal violet, and plaques counted.

Figure 1:
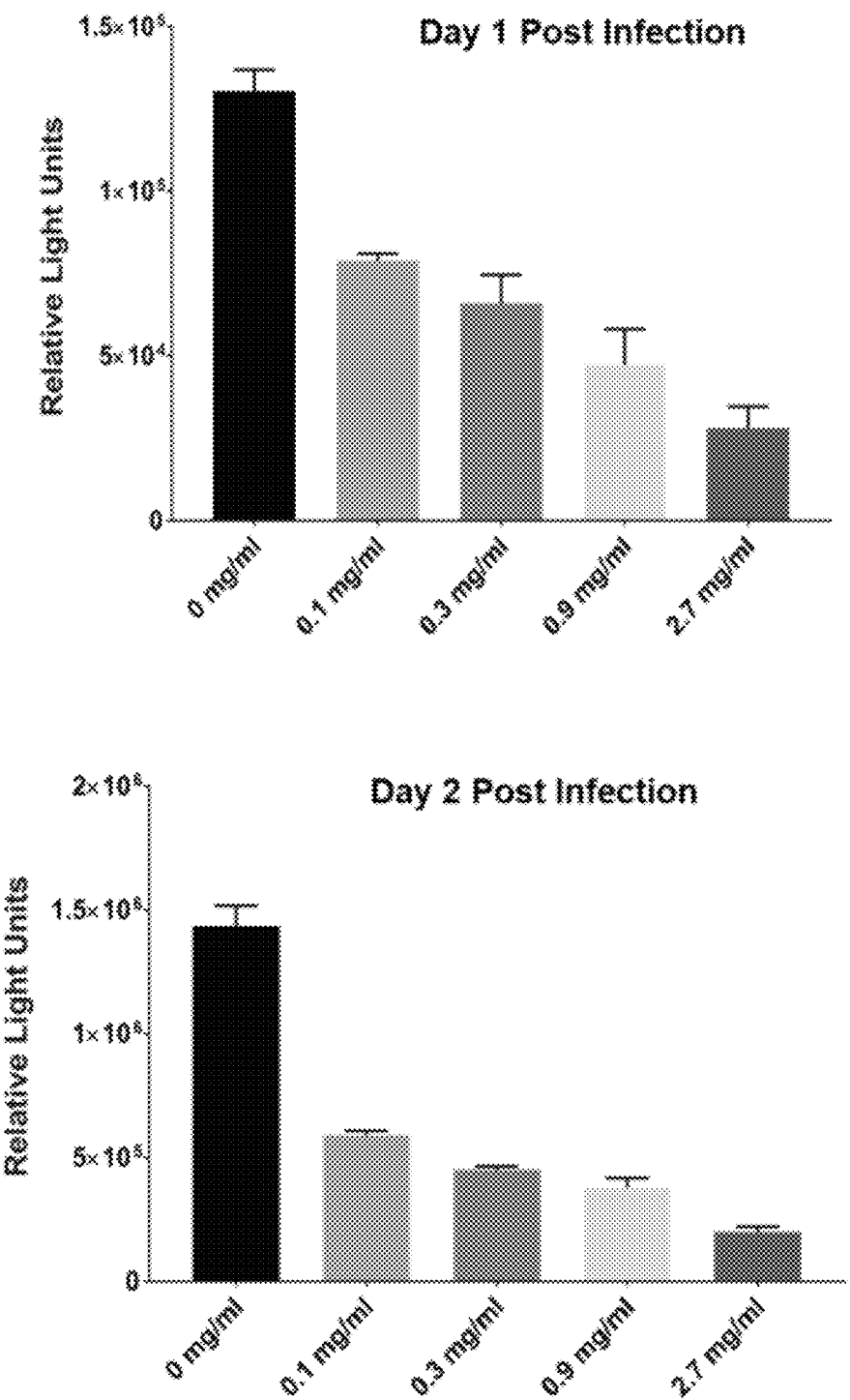
Figure 2:
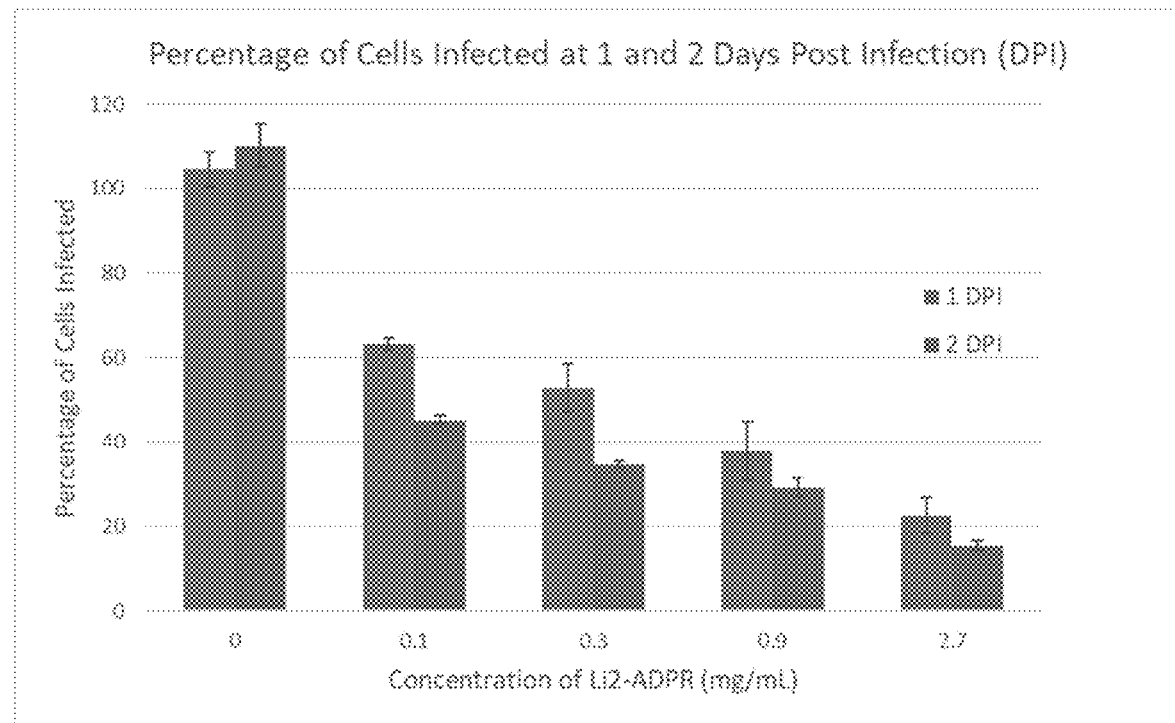
Figure 3:
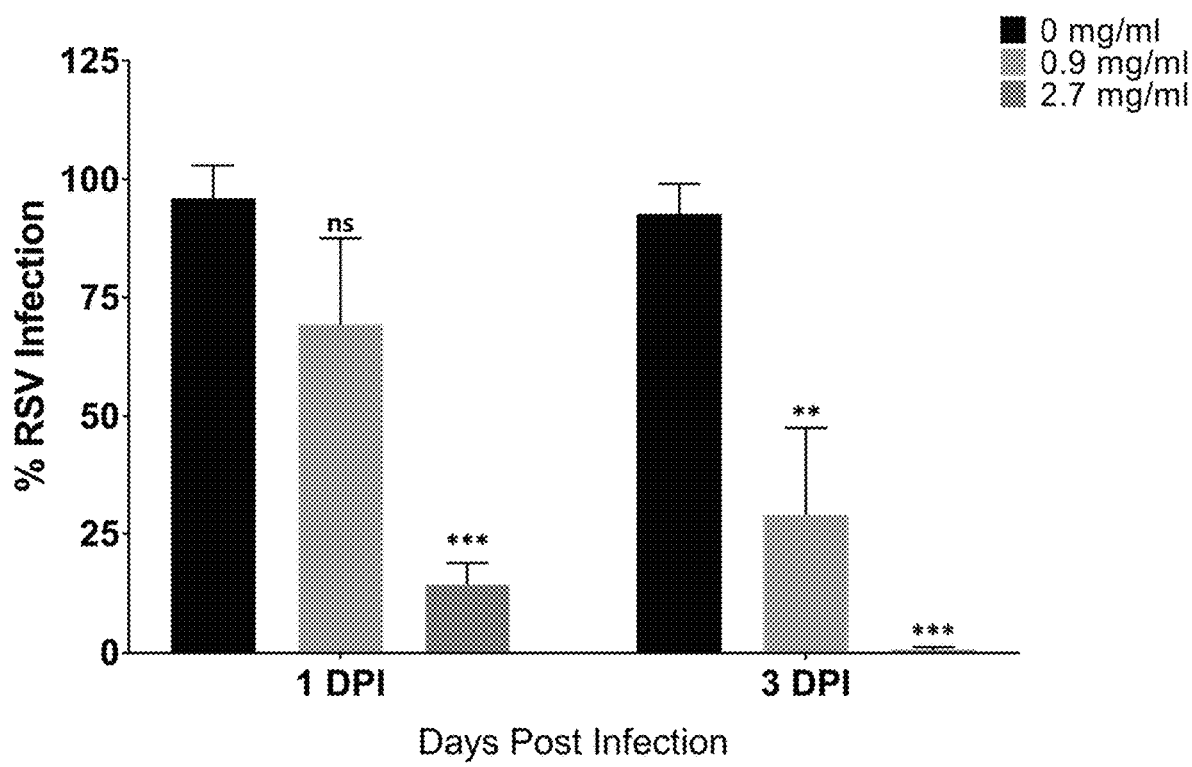
Figure 4:
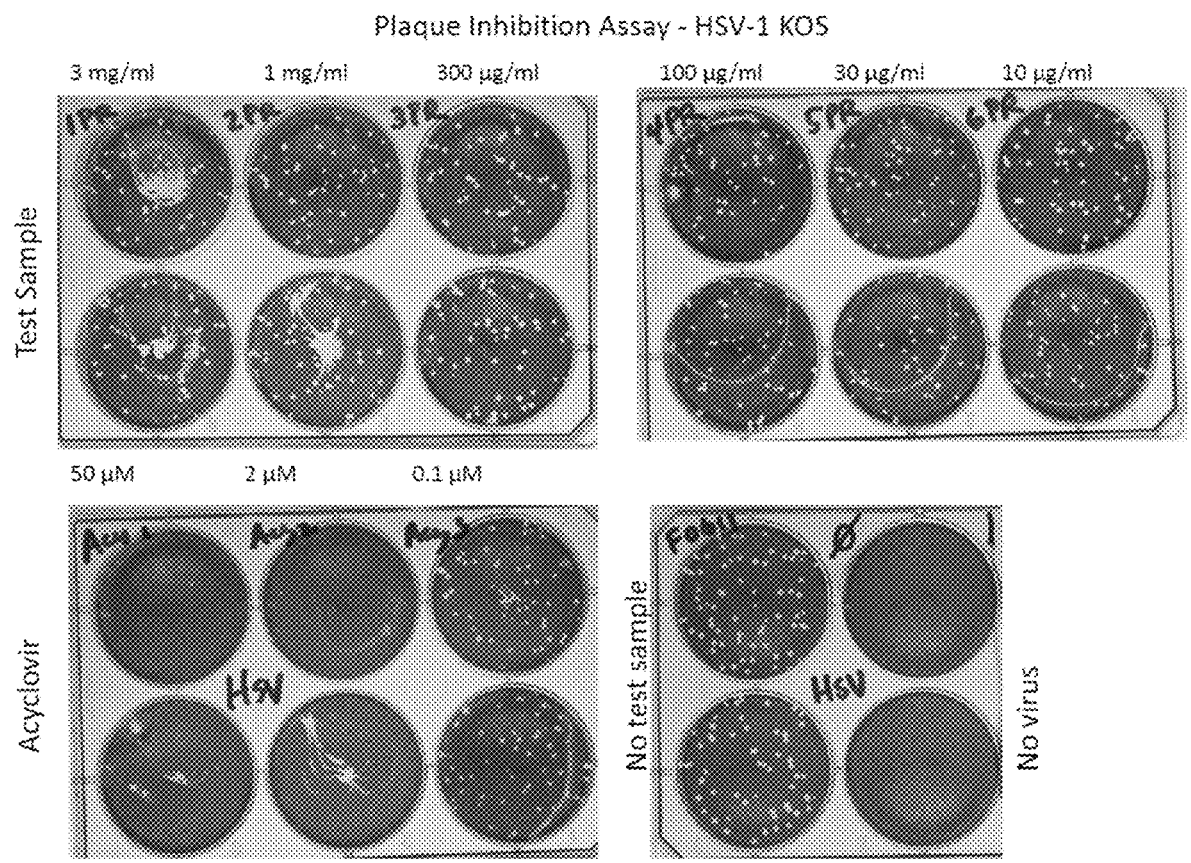

See plaque counts in Table 2 and plate images in FIG. 4.

Toxicity: Toxicity was evaluated against the below criteria and recorded in Table 2, and used to assess the effects of the dilutions of Sample on cell monolayers at the termination of the assay on the end day.

0—No Cytotoxicity
1—Slight Thinning of Cells compared to Cell Control wells
2—Moderate thinning of cells compared to Cell Control wells, moderately less intense staining of cells compared to Cell control wells, viral plaques are visible
3—Extreme thinning of cells compared to Cell Control wells to no cells present, extremely less intense staining of cells compared to Cell Control wells to no staining due to lack of cells, viral plaques are not visible.

Results: There was inhibition of plaque number and plaque size at the highest Sample dilution 3 mg/ml, with lesser effects at lower concentrations. The monolayer was not affected as judged under the microscope by 3 mg/ml Sample dilution prior to fixation, but was somewhat friable and detached when the agarose layer was flicked off.

TABLE 2

Plaque counts for HSV-1

| Sample Concentration | HSV-1 Raw Plaque Counts | Toxicity Grade on Vero Cells |
|---|---|---|
| 3 mg/ml | 39, 47 | 0 |
| 1 mg/ml | 51, 42 | 0 |
| 300 µg/ml | 56, 51 | 0 |
| 100 µg/ml | 51, 54 | 0 |
| 30 µg/ml | 57, 35 | 0 |
| 10 µg/ml | 60, 46 | 0 |
| No Sample | 64, 56 | 0 |
| Acyclovir Control HSV-1 | | |
| 50 µM | 0, 0 | 0 |
| 2 µM | 0, 0 | 0 |
| 0.1 µM | 56, 53 | 0 |

Control Drugs. The control drug (acyclovir) and concentrations used are listed in Table 2.

6.5 Example 6.5 Sirt6 Activation by Liz-ADPR

Previous studies (Pan et al., 2011, J. Biol. Chem., 286 (16):14575-14587) have indicated that ADPR, as a distinct entity, forms during the enzymatic reaction wherein the Sirt6-dependent histone deacetylation reaction produces O-acetyl-ADPR from nicotinamide-adenine-dinucleotide (NAD+) and the acetyl group attached to the lysine side chain of a protein or peptide substrate.

In keeping with the above observations, previous reports have indicated that ADPR inhibits Sirt6 deacetylation activity at concentrations greater than 1 mM (see Sirt6 assay published by Cerep/Eurofins with reference to Michishita et al., 2008, Nature, 452(7186):492-496). In addition, ADPR has been shown to inhibit the deacetylation reaction of a related sirtuin (Khan and Lewis, 2005, J. Biol. Chem., 281(17), 11702-11711.) known as Hst2. Hst2 is the yeast homolog of Sirtuin 2, and it has been the subject of structural, mutagenesis, and kinetic studies given its high degree of conservation and in vitro catalytic activity. In vivo, Hst2 appears to play similar roles as Sirtuin 2.

However, in eukaryote cells (Heiner, 2006, Biochem. J., 398(2):225-232), unbound ADPR concentrations are approximately 5 µM, and concentrations in the nucleus (Sirt6 protein resides almost exclusively in the nucleus) are likely to be considerably lower.

Figure 5:
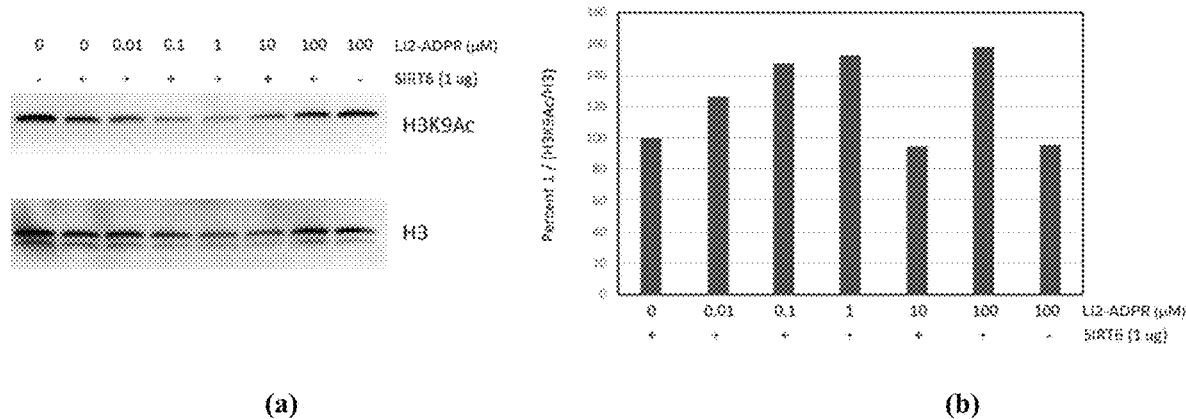

In contrast to what has previously been described, it has been surprisingly discovered that at low concentrations, ≤1 µM, ADPR increases Sirt6 activity. This was demonstrated in two sets of studies. This first set of studies was performed using a Western blot method (Rahnasto-Rilla, 2016, Methods Mol. Biol., 1436:259-269) for the in vitro evaluation of Sirt6 deacetylation activity. Serially diluted concentrations of $Li_2$-ADPR were incubated for 30 min at 37° C. in the presence of 1 µg/well of a purified recombinant GST-SIRT6 protein, 2 µg purified whole chicken core histones with 500 µM NAD+ in 25 mM Tris-HCl, pH 8.0. Acetylation level was detected with anti-H3K9Ac antibody and normalized to total H3 histone (FIG. 5(*b*)). Values indicate final $Li_2$-ADPR concentration in micromoles per liter (µM). The results (FIG. 5) demonstrate increasing activation of Sirt6 deacetylation activity between 0.01 and 1 µM, with variable activity at concentrations of 10 µM and above.

Figure 6:
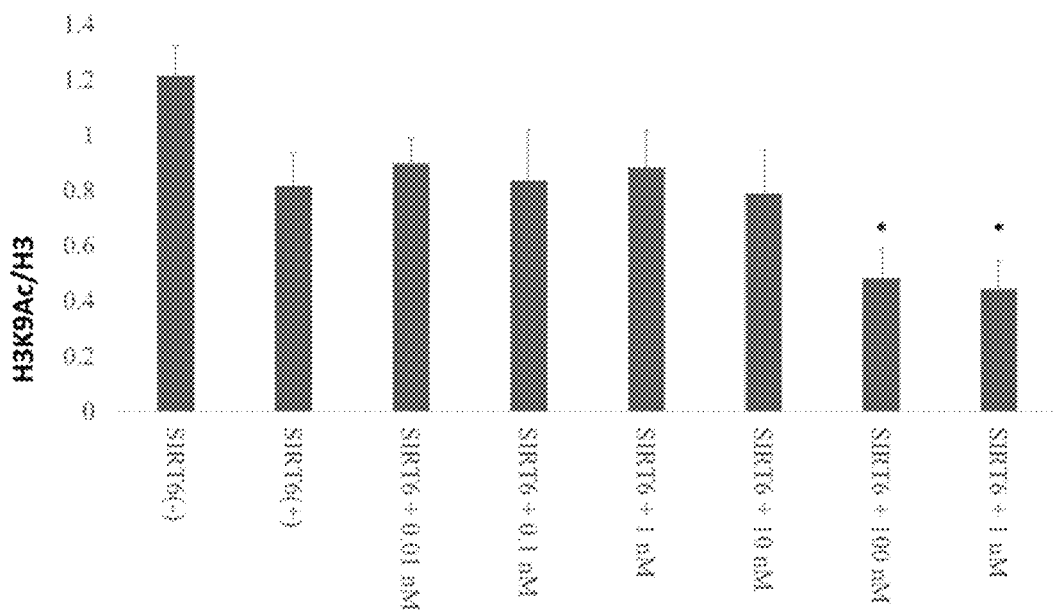
FIG. 6 shows the mean results of the Sirt6 activation study with $Li_2$-ADPR concentrations between 0.01 nM and 1000 nM (0.00001 μM and 1 μM).

This study was then repeated focusing on lower ranges of $Li_2$-ADPR concentrations. In the repeat study, the ratio of H3K9Ac to total H3 (shown on the vertical axis of FIG. 6 as H3K9Ac/H3) was significantly reduced at 0.1 and 1 µM. The second experiment was repeated three times (FIG. 6) and definitively proved that $Li_2$-ADPR concentrations between 0.1 and 1 µM increase the rate of Sirt6 deacetylation activity.

6.6 Example 6.6 Sirt6 Expression

Sirt6 expression using western blots was evaluated in human corneal epithelial cells.

Cell Culture: Human corneal epithelial cells (ATCC) were grown to just below confluency (80-90%) at 37° C., 5% $CO_2$. They were washed twice with sterile phosphate buffered saline (PBS) and serum starved for 2 hours at 37° C. Serum starvation media was aspirated and cells were treated with corresponding $Li_2$-ADPR treatment at 60 µM in serum starvation media. They were incubated for either 15, 30, 60 or 120 minutes with treatment. After each time point, treatment was aspirated and cells were washed twice with ice cold PBS. Cells were lysed in ice-cold cell lysis buffer and rotated end-over-end at 4° C. for 30 minutes. They were then centrifuged at 14,000 g for 30 minutes at 4° C. Supernatants were collected and total protein concentration for each sample was measured using spectrophotometric methods. Samples were stored frozen at -20° C. until performing the Western Blot.

Western Blot: Samples were prepared in 2× Laemmli sample buffer and boiled at 95° C. for 5 minutes. 20 µg protein was loaded into each lane of an 8% tris-glycine gel. Proteins are electrophoresed at 125V for approximately 50 minutes then transferred to nitrocellulose. After blocking the blot for 1 hour at room temperature in 3% BSA in a standard mixture of tris-buffered saline and Polysorbate 20 (TBST), primary antibody (anti-Sirtuin 6) was added in blocking buffer and incubated overnight at 4° C. The blot was washed 3 times with TBST and HRP-linked secondary antibody added at 1:2000 for 40 minutes at room temperature. The blot was again washed 3 times with TBST and developed with ECL reagents for 1 minute. Images were obtained with ChemiDoclt Imager (UVP, Upland Calif.) with exposures ranging from 30 seconds to 5 minutes. Image analysis were done with VisionWorks Software (UVP, Upland Calif.).

Figure 7:
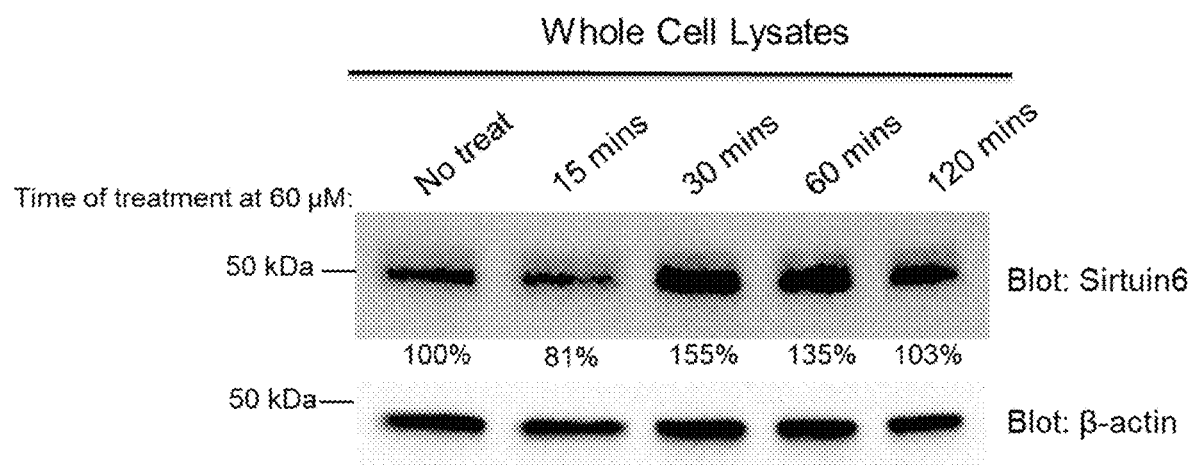
FIG. 7 shows the time dependent increase in protein concentration for Sirt6 in human corneal epithelial cells incubated with $Li_2$-ADPR at 60 μM.

The western blot results demonstrate that Sirt6 protein concentration was increased relative to baseline (No Treat lane) to 155% at 30 minutes and 135% at 60 minutes of incubation with $Li_2$-ADPR at 60 µM. Sirt6 protein concentration then returned to baseline by two hours. The results are shown in FIG. 7.

6.7 Example 6.7 Pax6 and Cytokeratin 12 Expression

Cell Culture: Using a nearly identical method to that described for Sirt6 expression, Pax6 and cytokeratin 12 expression were evaluated in human corneal epithelial cells (ATCC). Cells were grown to just below confluency (80-90%) at 37° C., 5% $CO_2$. They were washed twice with sterile phosphate buffered saline (PBS) and serum starved for 2 hours at 37° C. Serum starvation media was aspirated and cells were treated with corresponding $Li_2$-ADPR treatment at 60 µM in serum starvation media. They were incubated for either 15, 30, 60 or 120 minutes with treatment. After each time point, treatment was aspirated and cells are washed twice with ice cold PBS. Cells were lysed in ice-cold cell lysis buffer and rotated end-over-end at 4° C. for 30 minutes. They were then centrifuged at 14,000 g for 30 minutes at 4° C. Supernatants were collected and total protein concentration for each sample was measured using spectrophotometric methods. Samples were stored frozen at -20° C. until performing the Western Blot.

Western Blot: Samples were prepared in 2× Laemmli sample buffer and boiled at 95° C. for 5 minutes. Forty µg protein were loaded into each lane of an 8% tris-glycine gel. Proteins are electrophoresed at 125V for approximately 50 minutes then transferred to nitrocellulose. After blocking the blot for 1 hour at room temperature in 3% BSA in a standard mixture of tris-buffered saline and Polysorbate 20 (TBST), primary antibody (anti-Pax6 or anti-cytokeratin 12) was added in blocking buffer and incubated overnight at 4° C. The blot was washed 3 times with TBST and HRP-linked secondary antibody added at 1:2000 for 40 minutes at room temperature. The blot was again washed 3 times with TBST and developed with ECL reagents for 1 minute. Images were obtained with ChemiDoclt Imager (UVP, Upland Calif.) with exposures ranging from 30 seconds to 5 minutes. Image analysis was done with VisionWorks Software (UVP, Upland Calif.).

The western blot results demonstrate that Pax6 protein (isoforms 5a and 6) concentration was increased dramatically relative to baseline (No Treat lane). For the isoform 5a, protein concentration increased to 188% at 30 minutes and 584% at 60 minutes of incubation with $Li_2$-ADPR at 60 µM. For the isoform 6, protein concentration increased to 179% at 30 minutes and 302% at 60 minutes of incubation with $Li_2$-ADPR at 60 µM. Both isoforms decreased somewhat at two hours with isoform 5a at 206% and isoform 6 at 197% of baseline. Cytokeratin 12 was also evaluated. Both the monomer and dimer forms of cytokeratin 12 were increased at 30, 60, and 120 minutes relative to baseline. The monomer form was at 269% at 30 minutes, 789% at 60 minutes, and 505% at 120 minutes. The dimer form of cytokeratin 12 was at 139% at 30 minutes, 219% at 60 minutes, and 201% at 120 minutes. The results are shown in FIG. 8.

6.8 Example 6.8 ADPR Inhibits MDM2 Thereby Increasing p53

Cell Culture: Using a nearly identical method to that described for Sirt6 expression, p53 expression was evaluated in Human corneal epithelial cells (ATCC). Cells were grown to just below confluency (80-90%) at 37° C., 5% $CO_2$. They were washed twice with sterile phosphate buffered saline (PBS) and serum starved for 2 hours at 37° C. Serum starvation media was aspirated and cells were treated with corresponding $Li_2$-ADPR treatment at 60 μM in serum starvation media. They were incubated for either 15, 30, 60 or 120 minutes with treatment. After each time point, treatment was aspirated and cells are washed twice with ice cold PBS. Cells were lysed in ice-cold cell lysis buffer and rotated end-over-end at 4° C. for 30 minutes. They were then centrifuged at 14,000 g for 30 minutes at 4° C. Supernatants were collected and total protein concentration for each sample was measured using spectrophotometric methods. Samples were stored frozen at −20° C. until performing the Western Blot.

Western Blot: Samples were prepared in 2× Laemmli sample buffer and boiled at 95° C. for 5 minutes. Twenty μg protein were loaded into each lane of an 8% tris-glycine gel. Proteins are electrophoresed at 125V for approximately 50 minutes then transferred to nitrocellulose. After blocking the blot for 1 hour at room temperature in 3% BSA in a standard mixture of tris-buffered saline and Polysorbate 20 (TBST), primary antibody (anti-p53) was added in blocking buffer and incubated overnight at 4° C. The blot was washed 3 times with TBST and HRP-linked secondary antibody added at 1:2000 for 40 minutes at room temperature. The blot was again washed 3 times with TB ST and developed with ECL reagents for 1 minute. Images were obtained with Chemi-DocIt Imager (UVP, Upland Calif.) with exposures ranging from 30 seconds to 5 minutes. Image analysis was done with VisionWorks Software (UVP, Upland Calif.).

Results: The western blot results demonstrate that p53 protein concentration was rapidly increased relative to baseline (No Treat lane). Protein concentration increased to 313% at 15 minutes, 535% at 30 minutes, 407% at 60 minutes, and 510% at 120 minutes of incubation with Lie-ADPR at 60 μM. The results are shown in FIG. 9. This result definitively demonstrated that ADPR increased protein concentrations of p53, and therefore p53's activation. Once p53 activation was demonstrated, binding of ADPR to MDM2 was evaluated. It is known that MDM2 is the primary inhibitor of p53 activation, and it had been previously published that the purine compounds ATP (adenosine triphosphate) and ADP (adenosine diphosphate) bind to MDM2 in its ring finger domain (Poyurovsky et al., 2003, Molecular Cell, 12(4), 875-887; and Priest et al., 2010, Nucleic Acids Research, 38(21), 7587-7598). Analysis of ADPR binding with MDM2 was undertaken using Swissdock, a protein-small molecule docking web service based on EADock DSS (Grosdidier et al., 2011, Nucleic Acids Research, 39(SUPPL. 2), 270-277). Two previously developed protein models that are publicly available were used for docking. The first analysis evaluated docking of ADPR to the MDM2-MDMX ring domain heterodimer (Linke et al., 2008, Cell Death and Differentiation, 15(5), 841-848). ADPR was successfully docked in the cleft between the protein chains for MDM2 and MDM4 (FIG. 10 (a)). Maximum deltaG (free energy of binding) was −10.58 kcal/mol, which was consistent with the hypothesis that ADPR could inhibit the activity of the heterodimer, and thereby activate p53. Furthermore, ADPR was also shown to bind at the interface between MDM2 and p53 (FIG. 10 (b)). The protein structures used for this modeling were previously developed for analyzing small molecule benzodiazepinedione inhibitors of MDM2 which bind at the alpha helical transactivation domain of p53 (Grasberger et al., 2005, Journal of Medicinal Chemistry, 48(4), 909-912). When ADPR was docked with these proteins, it was found to bind to multiple sites in and around the transactivation domain. Though the maximum deltaG (−8.511 kcal/mol) was less than that observed for binding in the ring finger domain, the finding further indicated the potential for ADPR to inhibit MDM2's effect on p53.

6.9 Example 6.9 $Li_2$-ADPR Reduces Viral Titer and Modifies Cytokine Response in Cotton Rat RSV Lung Infection Methods: In view of the reduction in hRSV cellular infection in A549 and human airway epithelial cells, an in vivo experiment in the Cotton Rat was carried out using RSVA2 infection. In this study, adult male cotton rats (6-8 weeks of age) were divided into groups of 4 animals each. Animals were pre-bled for serum collection and ear tagged for identification. All animals were infected via intranasal instillation with 0.1 mL of RSV/A2 at $10^5$ plaque-forming units (pfu) per animal. The design of the study is shown in the following table:

| | | | Drug Treatment | | | RSVA2 infection | | |
| --- | --- | --- | --- | --- | --- | --- | --- | --- |
| Gp # | n | Drug | Dose | Vol/ Route | Study days | Amount (50 μL IN) | Study Day | Harvest Day |
| 1 | 4 | PBS | BID | 50 μL IN | 1 hr post infection and then BID through Day 4 | 1 × $10^5$ pfu | Day 0 | Day 5; |
| 2 | 4 | $Li_2$-ADPR | 0.5% soln, BID | 50 μL IN | | 1 × $10^5$ pfu | Day 0 | Collect serum and lung Titer lungs |

Animals were treated two times per day by nasal inhalation of either phosphate buffered saline or 0.5% $Li_2$-ADPR. At each treatment the animals received 50 μL. On day 5, the animals were sacrificed for viral lung titers and cytokine analysis. Interferon gamma (IFNγ) and transforming growth factor beta (TGFβ) gene expression were analyzed by PCR. The cytokine mRNA level was normalized relative to beta actin.

Results: On day 5, the RSV titers were reduced (FIG. 11 (a)) in the $Li_2$-ADPR treated animals and there was an increase in IFNγ with a significant decrease in TGFβ (see FIGS. 11 (b) and 11 (c) respectively).

6.10 Example 6.10 Effect of $Li_2$-ADPR on Plaque Inhibition Against HSV-1, Performed in A549 Cells Background: $Li_2$-ADPR was tested for effects on inhibition of HSV-1 virus plaque formation on A549 cells which are known to express moderate levels of both CD38 and CD157. Again, acyclovir was included as a positive control.

$Li_2$-ADPR was resolubilized to 100 mg/ml or a 175 mM solution in water for irrigation. This stock solution was used to generate the dilutions of the test sample. The following concentrations of Li$_2$-ADPR were evaluated: 0.1, 0.4, and 1.2 mM. Acyclovir was tested at 0.002 and 0.05 mM. A control, with no treatment was also evaluated.

Samples at the target concentrations per ml were added to A549 cell monolayers in duplicate in liquid virus growth media for one hour, and then approximately 100 plaque forming units of HSV-1, strain MacIntyre, were added to each monolayer. After virus adsorption, media was removed and monolayers overlaid with semisolid agarose media containing each drug dilution. Monolayers were fixed and stained with crystal violet to visualize virus plaques. Pictures of the test plates were submitted to client for image analysis.

Results: HSV 1 result—The no drug treatment (negative control) showed a monolayer of evenly spaced plaques of one size. The wells treated with 0.05 mM acyclovir showed few small breakthrough plaques. The wells treated with 0.002 mM Acyclovir showed more smaller plaques, but not as many nor as large as the untreated wells. The wells treated with 0.1 mM Li$_2$-ADPR showed plaques similar in number and size as the untreated wells, but as the drug concentration increased from 0.4 to 1.2 mM, the plaque number decreased and the plaque size decreased. FIG. 12 shows the effect of Li$_2$-ADPR on plaque inhibition against HSV-1.

Percent plaque area was calculated using ImageJ, version 1.52i. The results for Li$_2$-ADPR and the No Treatment Control are as follows:

| Li$_2$-ADPR | | | No Treatment |
|---|---|---|---|
| 0.1 mM | 0.4 mM | 1.2 mM | Control |
| 8.1% | 14.3% | 4.8% | 18.5% |
| 8.3% | 7.3% | 3.8% | 10.9% |

Though there was some variability at 0.4 mM, there was a clear decrease in percent plaque area as the concentration of Li$_2$-ADPR increased.

The invention claimed is:

1. A method for treating, managing, or preventing an RNA virus-related disease or condition in a patient, said method comprising administering to the patient an effective amount of 5'-adenosine diphosphate ribose (ADPR), or a pharmaceutically acceptable salt, solvate, hydrate, tautomer, stereoisomer, isotopologue, or polymorph thereof; wherein the patient has or is at risk of developing an RNA virus-related disease or condition; and
   wherein the RNA virus-related disease or condition is caused by an RNA virus, wherein the RNA virus is human respiratory syncytial virus (HRSV).

2. The method of claim 1, wherein the RNA virus-related disease or condition is epi-bulbar disease, conjunctivitis, keratitis, kerato-conjunctivitis, corneal abrasion, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, exacerbation of emphysema, or exacerbation of a chronic lung disease.

3. The method of claim 2, wherein the RNA virus-related disease or condition is conjunctivitis, keratitis, kerato-conjunctivitis, pharyngitis, tonsillitis, laryngitis, rhinitis, sinusitis, bronchitis, bronchiolitis, or pneumonia.

4. The method of claim 3, wherein the RNA virus-related disease or condition is keratitis, conjunctivitis, or kerato-conjunctivitis.

5. The method of claim 3, wherein the RNA virus-related disease or condition is bronchitis, bronchiolitis, or pneumonia.

6. The method of claim 3, wherein the RNA virus-related disease or condition is pharyngitis, tonsillitis, sinusitis, or laryngitis.

7. The method of claim 1, wherein the administering is done by topical, oral, parenteral, mucosal, or inhalation route of administration.

8. The method of claim 1, wherein the administering is done by inhalation administration.

9. The method of claim 7, wherein the topical administration is to an interior cellular or tissue surface of the patient.

10. The method of claim 9, wherein the topical administration is by aerosolization, nebulization, spray, oral delivery, intra-tracheal infusion, intra-bronchial, or infusion to a surface of the respiratory tract.

11. The method of claim 7, wherein the topical administration is to an exterior cellular or tissue surface.

12. The method of claim 11, wherein the exterior cellular or tissue surface is the surface of the skin, eye, nail, hair, or ear.

13. The method of claim 1, wherein the administering is done by intravenous, intra-arterial, or intraductal infusion.

14. The method of claim 1, wherein the patient is administered a pharmaceutical composition comprising ADPR, or a pharmaceutically acceptable salt, solvate, hydrate, tautomer, stereoisomer, isotopologue, or polymorph thereof, and an excipient, diluent, or carrier.

15. The method of claim 14, wherein the pharmaceutical composition is in the form of a solution, suspension, emulsion, microemulsion, nanoemulsion, suppository, enema, syrup, elixir, dry powder aerosol, liquid aerosol, tablet, or dissolving media.

16. The method of claim 15, wherein the dissolving media is a rapid dissolving tablet, film, or strip.

17. The method of claim 15, wherein the pharmaceutical composition is in the form of a solution.

18. The method of any one of claims 1 and 2-17, wherein the ADPR or pharmaceutical composition comprising ADPR is administered in combination with another medicament.

19. The method of claim 18, wherein the another medicament is an antiviral compound.

20. The method of claim 1, wherein the ADPR is in the form of its sodium salt.

21. The method of claim 1, wherein the ADPR is in the form of its disodium salt.

22. The method of claim 1, wherein the ADPR is in the form of its lithium salt.

23. The method of claim 1, wherein the ADPR is in the form of its dilithium salt.

* * * * *